US007769573B2

(12) United States Patent
Fejes et al.

(10) Patent No.: US 7,769,573 B2
(45) Date of Patent: Aug. 3, 2010

(54) SYSTEM AND METHOD FOR MODELING INTERACTIONS

(75) Inventors: Anthony Peter Fejes, Vancouver (CA); Ganesan Swaminathan, Surrey (CA); John Silvio Vieceli, Vancouver (CA)

(73) Assignee: Zymeworks Inc., Vancouver, BC (CA)

( * ) Notice: Subject to any disclaimer, the term of this patent is extended or adjusted under 35 U.S.C. 154(b) by 359 days.

(21) Appl. No.: 11/441,526

(22) Filed: May 26, 2006

(65) Prior Publication Data

US 2007/0276791 A1    Nov. 29, 2007

(51) Int. Cl.
*G06G 7/48* (2006.01)
*G06F 17/10* (2006.01)
(52) U.S. Cl. ............................... 703/6; 703/2
(58) Field of Classification Search ............... 703/6; 707/2
See application file for complete search history.

(56) References Cited

U.S. PATENT DOCUMENTS

| 5,625,575 | A | | 4/1997 | Goyal et al. | |
|---|---|---|---|---|---|
| 6,040,840 | A | * | 3/2000 | Koshiba et al. | 345/441 |
| 6,407,748 | B1 | * | 6/2002 | Xavier | 345/672 |
| 6,678,642 | B1 | * | 1/2004 | Budge | 703/2 |
| 2003/0187594 | A1 | | 10/2003 | Sherman et al. | |
| 2004/0009459 | A1 | * | 1/2004 | Anderson et al. | 434/262 |
| 2006/0129363 | A1 | * | 6/2006 | Shaw | 703/2 |

OTHER PUBLICATIONS

Beck, David A. C., et al., 2005, Cutoff Size Need Not Strongly Influence Molecular Dynamics Results for Solvated Polypeptides, *Biochemistry*, 44:609-616.

Brooks, Charles L. et al., 1985, Structural and Energetic Effects of Truncating Long Ranged Interactions in Ionic and Polar Fluids, *Journal of Chemical Physics*, 83:5897-5908.

Cheatham, T. E. et al., 1995, Molecular Dynamics Simulations on Solvated Biomolecular Systems: The Particle Mesh Ewald Method Leads to Stable Trajectories of DNA, RNA, and Proteins, *Journal of the American Chemical Society* 117:4193-4194.

(Continued)

*Primary Examiner*—Paul L Rodriguez
*Assistant Examiner*—Andre Pierre Louis
(74) *Attorney, Agent, or Firm*—Morgan, Lewis & Bockius LLP; Jeffry S. Mann; Tuan N. Nguyen

(57) ABSTRACT

Computerized systems and methods are used to create a model of interaction energies between a group of bodies, such as molecules or atoms in solution. A computer simulation of the molecular interactions of bodies in solution is performed by first creating a coordinate system that defines a position of each body in a two dimensional or a three-dimensional space. The system then divides the coordinate system into subsections called bins. Bins may be of different sizes. The number and size of bins varies depending on the number of bodies and each body's calculated position in the coordinate system. The number of bins is optimized, selected so that a maximum number of bins contain only one body. This means there is also a corresponding minimum number of bins that contain either multiple bodies or no bodies. The systems and methods select a radius at which, at a certain distance from a selected molecule, the effect of other molecules on the selected molecule approximates zero. The binning system thus computes all of the significant interactions between N bodies in a solution without missing interacting pairs of bodies and without testing every possible interaction.

19 Claims, 12 Drawing Sheets

OTHER PUBLICATIONS

Darden, T. et al., 1999, New Tricks for Modelers From the Crystallography Toolkit: the Particle Mesh Ewald Algorithm and its use in Nucleic Acid Simulations, *Structure with Folding and Design*, 7:R55-R60.

Darden, T. et al., 1993, Particle Mesh Ewald: An N•log(N) Method for Ewald Sums in Large Systems, *Journal of Chemical Physics*, 98:10089-10092.

Deserno, M. et al., 1998, How to Mesh up Ewald Sums. I. A Theoretical and Numerical Comparison of Various Particle Mesh Routines, *Journal of Chemical Physics*, 109:7678-7693.

Deserno, M. et al., 1998, How to Mesh up Ewald Sums. II. An Accurate Error Estimate for the Particle-Particle-Particle-Mesh Algorithm, *Journal of Chemical Physics*, 109:7694-7701.

Ding, et al., 1992, The Reduced Cell Multipole Method for Coulomb Interactions in Periodic Systems with Million-Atom Unit Cells, *Chemical Physics Letters*, 196:6-10.

Ding, et al., 1992, Atomic Level Simulations on a Million Particles: The Cell Multipole Method for Coulomb and London Nonbond Interactions, *The Journal of Chemical Physics* 97-4309-4315.

Essman, et al., 1995, A Smooth Particle Mesh Ewald Method, *Journal of Chemical Physics* 103:8577-8593.

Garemyr, et al., 1999, Study of the Electrostatics Treatment in Molecular Dynamics Simulations, *Proteins* 37:417-428.

Greengard, et al., 1987, A Fast Algorithm for Particle Simulations *Journal of Computational Physics*, 73:325-348.

Loncharich, et al. 1989, The Effects of Truncating Long-Range Forces on Protein Dynamics, *Proteins*, 6:32-45.

Lotan, et al., 2003, Efficient Energy Computation for Monte Carlo Simulation of Proteins, *Workshop on Algorithms for Bioinformatics* (WABI 2003).

Luty, et al., 1994, A Comparison of Particle-Particle, Particle-Mesh and Ewald Methods for Calculating Electrostatic Interactions in Periodic Molecular Systems, *Molecular Simulation* 14:11-20.

Luty, et al., 1995, Lattice-Sum Methods for Calculating Electrostatic Interactions in Molecular Simulations *Journal of Chemical Physics*, 103:3014-3021.

Plimpton S., 1995, Fast Parallel Algorithms for Short-Range Molecular Dynamics, *Journal of Computational Physics*, 117:1-19.

Quentrec, et al., 1973, New Method for Searching for Neighbors in Molecular Dynamics Computations, *Journal of Computational Physics*, vol. 13, 430-432.

Steinbach, et al., 1994, New Spherical-Cutoff Methods for Long-Range Forces in Macromolecular Simulation, *Journal of Computational Chemistry*, 15:667-683.

Thompson, S.M., 1983, Use of Neighbour Lists in Molecular Dynamics, *Collaborative Computational Projects* 5, 8:20-28.

Verlet L., 1967, Computer 'Experiments' on Classical Fluids. II. Equilibrium Correlation Functions, Physical Review 165:201-204.

York, et al., 1994, Atomic-Level Accuracy in Simulations of Large Protein Crystals, *Proceedings of the National Academy of Sciences USA* 91:8715-8718.

\* cited by examiner

| +1,+1 | +1,0 | +1,-1 |
|---|---|---|
| 0,+1 | 0,0 | 0,-1 |
| -1,+1 | -1,0 | -1,-1 |

FIG. 9

SYSTEM AND METHOD FOR MODELING INTERACTIONS

BACKGROUND OF THE INVENTION

1. Field of the Invention

This invention relates to systems and methods of determining interactions between bodies in a simulation space. More specifically, this invention relates to modeling interactions between molecules in solution.

2. Description of the Related Art

Molecular modeling belongs to a class of problems called N-body problems, where the behavior of each body in the system depends on its interaction with all of the other bodies in the system. Because it is impossible to calculate all of these interactions simultaneously, the only computational way to solve this problem is to loop over each possible pair of bodies, to determine how they affect each other. Thus, any selected body in a system containing N bodies requires looping over all of the other N-1 bodies to determine their affect on the selected body. In some embodiments the same process may then be repeated for all of the other N-1 bodies. Thus, there are $N*(N-1)$, or $N^2-N$ interactions, which is written in Big-O notation as $O(N^2)$.

A common modification made to algorithms for solving N-body problems includes using cut-off radii, in which the contribution to the interaction of the chosen body from bodies outside the range of a cut-off radius are considered insignificant.

Using this method, the distance between each body pair in the system is checked at every iteration. Although calculating the distance is a relatively cheap operation in terms of computational efficiency, the necessity of iterating over every possible combination of bodies can become computationally expensive. One commonly used method of reducing the amount of computational time required to find interacting pairs of bodies is to cache the list of those bodies that interact. See Verlet, *Computer 'Experiments' on Classical Fluids. II. Equilibrium Correlation Functions, Physical Review*, 165: 201-204 (1967), which is hereby incorporated by reference in its entirety.

One significant problem of using cached interacting pairs occurs because the list of cached interactions is not frequently updated. If the bodies change distances during or after an iteration, which is usually the case, the cached list of interacting bodies may not contain a full and accurate list of interacting pairs. The cached list may therefore lead to an inaccurate solution. Thus, a significant trade-off exists between the accuracy of the cached values and the frequency of the cache updates. Correcting this problem by updating the interaction table more often results in greater overhead (required to maintain the table) and a return to calculating all of the interactions (which were being avoided by the creation of the table). Caching infrequently creates situations in which the solution obtained may be inexact or incorrect.

One proposed solution includes widening the number of cached interactions to include non-interacting pairs, which may be expected to begin interacting within a certain number of iterations. Although the additional interactions that are being checked will slow down the iteration over the N atoms, this method reduces the number of full passes made through all possible interacting pairs. Further, this method does not solve the trade off between the cache and the update of the cache. See Thompson, *Use of Neighbour Lists in Molecular Dynamics, Collaborative Computational Projects*, 5, 8:20-28 (1983), which is hereby incorporated by reference in its entirety.

One available method to solve this problem is derived from a technique proposed based on spatially subdividing simulation space into separate equally-sized sections and then approximating a spherical cutoff by searching through a subsection of the subdivided areas. See Quentrec and Brot, New Method for Searching for Neighbors in Molecular Dynamics Computations, *Journal of Computational Physics*, 13:430-432 (1973), which is hereby incorporated by reference in its entirety. Although this technique did not demonstrate a significant gain in speed, it did show a reduction in memory usage. Further historical refinements to the method included a defined memory structure to improve access times for each subdivision and the cells contained. See Leach, *Molecular Modeling: Principles and Applications*, Addison Wesley Longman, Essex, England (1996), which is hereby incorporated by reference in its entirety. Still other approaches to these methods were based upon neighbor lists. See Verlet, supra; and Thompson, supra.

SUMMARY OF THE INVENTION

In one embodiment an optimized computerized method of determining interaction energies between bodies in a simulation space comprises providing a simulation space comprising a plurality of bodies, dividing the simulation space into subsections, wherein the number of subsections with only one body is maximized, selecting a radius for a first body in the simulation space at which an effect of a second body on the first body can be approximated to zero and calculating the interaction energy of all bodies within the radius on the first body.

In some embodiments the method further comprises assuming an even distribution of bodies. In some embodiments the method further comprises providing a cube of bins comprising 2k+1 bins in each direction from which the radius radiates. In some embodiments the method further comprises providing bins, wherein the bins are positioned to approximate a volume of a sphere with the radius. In some embodiments the method further comprises using a group based cutoff. In some embodiments the method further comprises using a switching function. In some embodiments the method further comprises moving bodies between bins. In some embodiments the method further comprises providing an iterator map. In some embodiments the method further comprises providing a relative map that may be applied to any cell and wherein only one map is stored and wherein the one map comprises a list of relative positions of all neighbor bins over which the iterator may pass.

In another embodiment a computer readable medium comprising computer executable instructions that cause a computer to perform a method for optimizing system performance of an N-body problem comprises providing a simulation space comprising a plurality of bodies dividing the simulation space into subsections, wherein the number of subsections with only one body is maximized, selecting a radius for a first body in the simulation space at which an effect of a second body on the first body can be approximated to zero and calculating the interaction energy of all bodies within the radius on the first body.

In some embodiments the computer readable medium further comprises assuming an even distribution of bodies. In some embodiments the computer readable medium further comprises providing a cube of bins comprising 2k+1 bins in each direction from which the radius radiates. In some embodiments the computer readable medium further comprises providing bins, wherein the bins are positioned to approximate a volume of a sphere with the radius. In some embodiments the computer readable medium further comprises using a group based cutoff. In some embodiments the computer readable medium further comprises using a switching function. In some embodiments the computer readable medium further comprises moving bodies between bins. In some embodiments the computer readable medium further comprises providing an iterator map. In some embodiments the computer readable medium further comprises providing a relative map that may be applied to any cell and wherein only one map is stored and wherein the one map comprises a list of relative positions of all neighbor bins over which the iterator may pass.

In another embodiment a computer system for modeling interactions between bodies comprises a first module configured to provide a simulation space comprising a plurality of bodies, a second module configured to divide the simulation space into subsections, wherein the number of subsections with only one body is maximized, a third module configured to select a radius for a first body in the simulation space at which an effect of a second body on the first body can be approximated to zero and a fourth module configured to calculate the interaction energies of all bodies within the radius on the first body.

In some embodiments of the computer system the simulation space comprises at least two dimensions. In some embodiments of the computer system the subsections are of equal shape. In some embodiments of the computer system the subsections are of equal volume. In some embodiments of the computer system the simulation space comprises non-cubic dimensions.

BRIEF DESCRIPTION OF THE DRAWINGS

FIG. 9 illustrates a relational map for a center cell in a 3×3 group of cubes.

DETAILED DESCRIPTION OF THE PREFERRED EMBODIMENT

Figure 1:
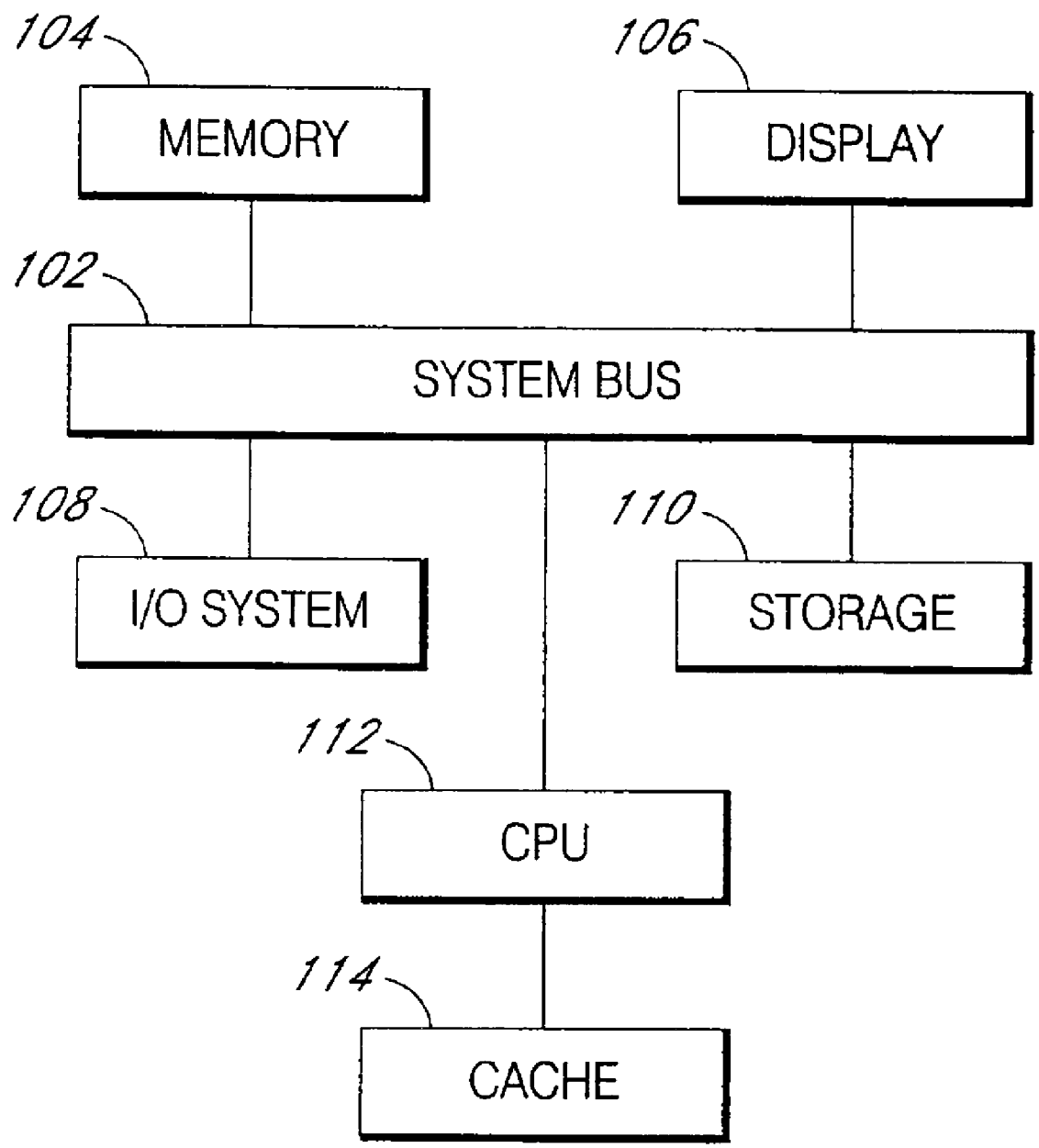
FIG. 1 shows a schematic diagram of a hardware system for performing one embodiment of a method of the present invention.

Embodiments of the invention relate to computerized systems and methods that determine interaction energies between multiple bodies. In one embodiment, one or more computers are used to create a model of interactions between a group of molecules or atoms in solution. In this embodiment, a computer simulation of the molecular interactions of the bodies in solution is performed by first creating a coordinate system that defines a position of each body in a two dimensional or a three-dimensional space. The system then divides the coordinate system into subsections called bins. In one embodiment the coordinate system is divided into bins of different sizes. The number and size of bins can vary depending on the number of bodies and each body's calculated position in the coordinate system. The number of bins is selected so that a maximum number of bins contain only one body. This means there is also a corresponding minimum number of bins that contain either multiple bodies or no bodies.

Each molecule in the solution interacts with other molecules in the solution. Those molecules nearest to a selected molecule have a greater interaction with the selected molecule than molecules further from the selected molecule. At a certain distance from the selected molecule, the effect of other molecules on the selected molecule approximates zero. That certain distance is selected as a radius from the selected molecule. The interactions of all molecules within the radius are then calculated for each molecule in the solution. Thus, the binning system computes all of the significant interactions between N bodies in a solution without missing interacting pairs of bodies, and without testing every possible interaction.

Thus, the principle binning method for determining interaction energies between bodies uses a computer to create a simulation space with a plurality of bodies. The computer divides the simulation space into bins. The number of bins is chosen so as to maximize the number of bins that contain only one body. The computer selects a radius for a first body in the simulation space at which an effect of a second body on the first body is approximately zero and then calculates the interaction energy of all bodies within the radius on the first body. Bodies that may be binned by the systems and methods described herein include, but are not limited to particles, atoms, molecules, celestial bodies, stars, animals, people, plants, trees, towns, and cities. Because N-body problems are a full class of problems, solving any one problem within the class indicates that any of them can be solved.

Thus, systems and methods described herein use a "binning layer" for applications that require an answer for the N-body problem without consuming $O(N^2)$ computational time. As explained above, a computer breaks down a single simulation space into "bins" of equal volume and/or equal shape, and allows one or more computer programs to retrieve, in $O(1)$ time, all of the bodies within a given radius ($r_{cutoff}$) from a specific point in the simulation space. This is particularly useful for molecular modeling applications.

By adjusting the dimensions of the bins, the body counts and the cutoff size, we have demonstrated that improved behavior can be obtained, when the number of bins into which the system is divided is adjusted for optimal performance. This allows the system to be optimized both in terms of the memory required, and in terms of performance gained.

The binning methods described herein optimize the number of bins required for best performance, while simultaneously minimizing the number of empty bins in the solution space. Because checking to determine if a particular bin is empty does not require much more overhead than checking if the current body is the last body in the bin, the binning method provides better performance than previous techniques.

Description of the System

FIG. 1 shows a schematic diagram of a modeling system 100 for performing the method of the present invention. The hardware system 100 includes a system bus 102 comprising a memory 104, a display 106, an I/O system 108 and a storage 110. The I/O system 108 is a network interface that allows for input and output of information. The storage 110 stores the data being processed by the system. The system bus 102 is also connected to a CPU 112 (a Central Processing Unit that processes the data in the system), and a cache 114. Thus, the system may be used to obtain information about a simulated system, process information, store the information and then retrieve and return the information. Additionally, a number of modules can be present in the system.

As used herein, the term "module" refers to the various modules in the system as discussed in detail below. As can be appreciated by one of ordinary skill in the art, each of the modules comprises various sub-routines, procedures, definitional statements and macros. Modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Scaling

One advantage of the binning method is the speed with which it is able to solve N-body problems, however, this difference in speed can be quantified to show that it has an advantage over similar methods. Thus, understanding the scaling behavior allows the device to be optimized in order to achieve the best possible performance. The method used by the binning method has a complex scaling behavior, dependent on other variables than just the number of bodies in the system. An equation (that will be introduced and explained further below) can be used to quantify the performance of the system with respect to the $r_{cutoff}$, $l^{system}$, o and N parameters.

In one embodiment, the binning method uses at least three input parameters: "$l^{system}$", "$r_{cutoff}$" and "o". The parameter $l^{system}$ represents the length of one dimension of the simulated system space. For cases in which more than one dimension are used, a vector $l^{system}$ is used. For example, when the system being simulated is a three dimensional cube, $l^{system}$ will be equal in all three dimensions, $l_x^{system} = l_y^{system} = l_z^{system}$. When the simulated system is not a three dimensional cube $l^{system}$ may be different in every dimension.

The parameter $r_{cutoff}$ represents the cutoff distance at which the longest range force can be approximated to zero. This is a property of the simulation system itself, although it may be adjusted by the user of the simulation to increase the precision of the simulation to a maximum of one half of the length of the smallest dimension of the system. For notation purposes, $r_{cutoff}$ can also be written as the vector k, which describes set of k parameters in each dimension.

$$k = \text{ceil}\left(\frac{r_{cutoff}}{l^{bin}}\right) \quad (1)$$

Because of the relationship between $l^{bin}$, and the order and length of the system itself, $$l^{bin} = \frac{l^{system}}{o} \quad (2)$$

the value of k can also be calculated from the system parameters as:

$$k = \text{ceil}\left(\frac{r_{cutoff} \cdot o}{l^{system}}\right) \quad (3)$$

k always describes the depth in the number of bins between the center cell and the distance $r_{cutoff}$ in each dimension. The ceil function is required to include entire bins, when any part of the bin falls within the $r_{cutoff}$ radius from the center bin.

The parameter o is the order of the simulation, which is defined as the number of bins required in each dimension of the system to make up the length $l^{system}$ in that dimension. As with $l^{system}$, the order does not necessarily need to be identical in each dimension, and can be represented by $o_x$, $o_y$, and $o_z$ or the equivalent vector o. (In either notation, the o is always an integer value.) Nevertheless, optimal performance is often achieved by systems where o is identical or similar in each dimension (for example, [$o_x$, $o_y$, $o_z$]=[5,5,5] or [20,19,20]), or when the systems are rectangular (for example, [$o_x$, $o_y$, $o_z$]= [24, 18, 24]).

Thus, the $r_{cutoff}$ parameter describes the maximum distance at which two bodies may interact. This parameter is isotropic, and thus has no directional components. It integrates into the binning system by defining the area or volume within the distance $r_{cutoff}$ from a given bin, and allows for the creation of a list encompassing all bins which may contain interacting bodies. In the simplest form of binning, $r_{cutoff}$ is approximated by a cube constructed of bins, with each edge of the cube being at least 2 times $r_{cutoff}$ plus the size of one bin.

Figure 2:
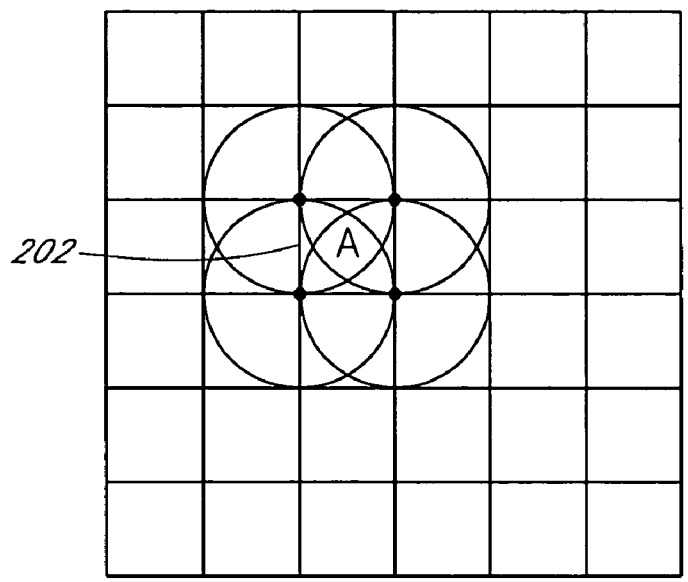
FIG. 2 illustrates a bin with an $r_{cutoff}$ value equal to the length of a bin.

FIG. 2 shows a sample simulation space 200 divided into square bins. The number of bins in each dimension that are required to make up the distance specified by $r_{cutoff}$, is given the parameter k, which is independent in each dimension. The center bin 202 is marked with an "A" and the $r_{cutoff}$ value is equal to the length of a bin, thus k=1. As in this example, where $r_{cutoff}$ is equal to the length of one side of a bin, each of the bodies at the corners of the bin A sweeps an area such that the bodies in the area will be within the $r_{cutoff}$ radius. All neighboring bins may contain bodies that interact with bodies in the center bin. For small systems, as the one shown, the efficiency of the binning method is a poor approximation both because the binning method can return all the bodies that could be within the $r_{cutoff}$ radius and because the method does not take into account an actual location of a body at the center of the $r_{cutoff}$ radius within the bin A 202.

Thus, because it is possible for bodies to be at each of the four corners of the center bin, all bins within the $r_{cutoff}$ radius of each corner can be taken into account. Once all points inside the bin A 202 are covered, all of the space within a distance of $r_{cutoff}$ from the bin A 202 may be interacting with bodies in the bin.

Figure 3:
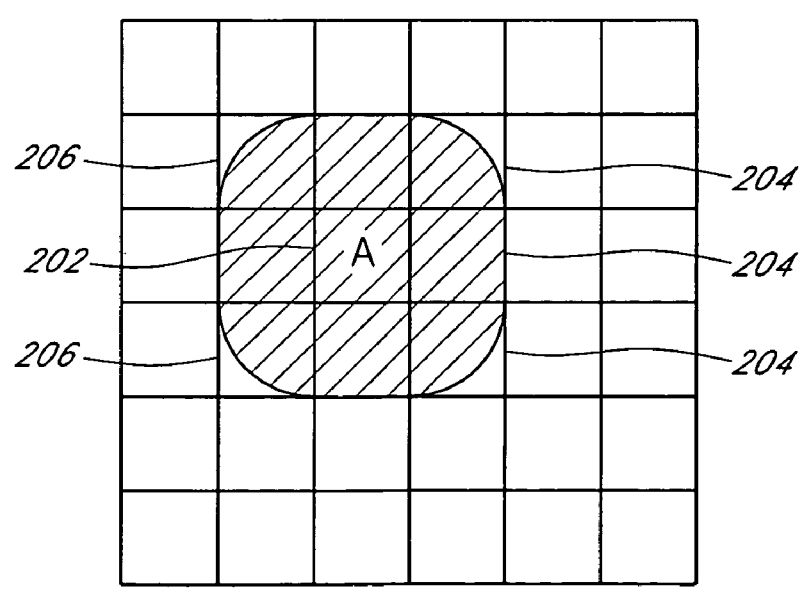
FIG. 3 illustrates a square with rounded corners representing the area covered by the $r_{cutoff}$ Radii extending from any point in the center bin A.

FIG. 3 illustrates the effect of the method of FIG. 2 on the simulation space 200. A body may exist anywhere within bin A 202. The binning method can therefore return the set of all bodies (the set includes those bodies in all neighboring bins) that interacts with a selected body. The total area encompassed by $r_{cutoff}$ when $r_{cutoff}$ is equal to the length of one side of a bin (the area extending a maximum distance from any point within the square bin A 202 within which the selected body may be found) resembles a square with rounded corners.

Whole numbers of bins are used to cover the area 204 within the $r_{cutoff}$ radius. Thus, every bin in which any portion is included within the $r_{cutoff}$ distance from bin A 202 (containing the selected body) is considered in its entirety. Thus, in FIG. 3, the entire contents of the four bins 206 that fall underneath the rounded corners of the area 204 swept by the $r_{cutoff}$ radius are considered as if they were completely encompassed by the area 204 within the $r_{cutoff}$ distance from bin A 202.

Usage of the Binning Method Interface

To use the binning method, the device itself is initialized, and once the usage is complete, a cleanup process is typically started. The cleanup process allows for the device itself to be re-used, without a restart. This practice is implemented in the software portion of the binning method.

The initialization of the binning method normally includes three steps;

1. The creation of the bins,
2. The creation of the iterator's map,
3. The placement of bodies into their proper bins.

The creation of the bins uses the parameter $o_i$ to determine number of bins that the simulation space will be divided into, followed by the allocation of memory for the bin's components. The number of bins, using cubic or rectangular prismatic bins, can be found by multiplying the order, o, in each dimension, $$M_{bins} = \prod_{i=x,y,z...} o_i \qquad (4)$$

The first step in creating the bins is to allocate sufficient contiguous memory to hold the pointers to each bin, or create an array of pointers, one for each of the $M_{bins}$ bins. Each bin then has internal structures, which includes sufficient memory to hold all of the bodies contained by the bins. If the bodies are stored in other arrays, the bin may store only indices to the locations of the bodies in the arrays in which they are contained. For bins containing relatively small numbers of bodies, a linked list approach can be used for storing the bodies within the bins. The linked list can be allocated in contiguous memory if the number of bodies in the system is static. The code required for this operation is found in Appendix B, in function bin_init( ). See Allen and Tildesley, *Computer Simulation of Liquids*, Oxford University Press, Oxford, p. 151 (1987); Knuth, *The Art of Computer Programming* (2nd ed.), Addison-Wesley, Reading, Mass. (1973); and Hockney and Eastwood, *Computer Simulation Using Particles*, McGraw-Hill, New York, chapter 8 (1981), which are hereby incorporated by reference in their entireties.

As part of the initialization process, the creation of the map, used to determine which bins fall within the cutoff distance from any other bin, can then be performed. This map stores the relative positions of each bin. The code used to create the map can be found in the private function bin_map_init( ) in Appendix B.

This binning map, which is the relative directions in bins, can be converted to absolute bin numbers, as long as a unique bin identifier is given as a starting point, and vice versa. These functions, however, are not required to be performed by the user since the iterator function automates these tasks. Thus, the functions for performing these tasks are private (only accessible to the binning method). They can be found in Appendix B, as functions bin_map_ijk2int( ) and bin_map_int2ijk( ).

In order to understand the scaling behavior of the underlying binning algorithm used by the binning method, the cubic approximation method can be used, providing a relatively simple outcome. The spherical approximation follows the same behavior with a multiplier that tends towards $\pi/6$ as the k value increases.

Calculating the Number of Bins Required

For the cubic binning approximation, where a cubic volume is used to approximate the volume described by the $r_{cutoff}$, the number of bins that are used to approximate this value is represented by the symbol $M_{bin}$. This quantify can be found for a cubic binning system by the equation $$M_{bin} = (2k+1)^D \qquad (5)$$

where D is the number of dimensions used in the system. In the two dimensional system, this expands to $$M_{bin} = 1 + 4k + 4k^2 \qquad (6)$$

which is easily visualized. For a three dimensional system, this can be expanded to $$M_{bin} = 8k^3 + 12k^2 + 6k + 1 \qquad (7)$$

where the 1 refers to the center cell, in which the body of interest resides, the 6k bins refer to the bins along the axes, the $12k^2$ bins refer to planes between the bins along the 6 axes, and the $8k^3$ bins refer to the cubes in each corner.

From equation (2), the size of the bins in each dimension can be determined from the $l^{system}$ and o parameters. This allows the volume of each bin to be calculated by multiplying the length in each dimension, represented by i.

$$V_{bin} = l_x^{bin} \cdot l_y^{bin} \cdot l_z^{bin} \qquad (8)$$

In the cubic binning approximation method, the volume of $r_{cutoff}$ is made from a cube of bins, of which $M_{bins}$ are required, which gives the volume of interaction for each bodies as:

$$V_{r_{cutoff}}^{cubic} = V_{bin} \cdot M_{bins} \qquad (9)$$

Thus, by substituting back to our fundamental variables, r, o and $l^{system}$, by using equations (3) and (4), and expanding to show each of the three dimensions, you can obtain the volume of the system space with which each body interacts using the cubic approximation.

$$V_{r_{cutoff}}^{cubic} = \frac{l_x^{system}}{o_x} \cdot \left(2\left(\text{ceil}\left(\frac{r_c \cdot o_x}{l_x^{system}}\right)\right) + 1\right) \cdot \frac{l_y^{system}}{o_y} \cdot \\ \left(2\left(\text{ceil}\left(\frac{r_c \cdot o_y}{l_y^{system}}\right)\right) + 1\right) \cdot \frac{l_z^{system}}{o_z} \cdot \left(2\left(\text{ceil}\left(\frac{r_c \cdot o_z}{l_z^{system}} + 1\right)\right)\right) \qquad (10)$$

The greater the difference between this volume and the system volume is, the more efficient the scaling behavior observed will be.

In addition to the user defined properties, the binning method's behavior also depends upon N, the number of atoms in the system. The more sparse the system, the fewer inter-body interactions will need to be calculated. Because each system has N bodies, and every body needs to interact with every other body, there are a maximum of $N^2$ interactions that can be calculated. In a system where an $r_{cutoff}$ parameter can be specified, some interactions can be ruled out because of their distance is greater than $r_{cutoff}$. Thus, this device, which is able to provide a method of eliminating the majority of interactions over distances greater than $r_{cutoff}$, is able to reduce the number of interactions below the maximum number of $N^2$.

Assuming that the bodies are distributed evenly through the system bins, the ratio of the space included in possible interactions to the total volume of the simulation space provides the scaling behavior of this algorithm. Using different methods for deriving the scaling behavior of this device also yield the same equation:

$$\text{Scaling} = \frac{N^2 \cdot V_{interaction}}{l_x^{system} \cdot l_y^{system} \cdot l_z^{system}} \quad (11)$$

If the volume described by $V_{interaction}$ were ideal, that is to say that the bins were able to exactly match the volume of space within of $r_{cutoff}$ exactly for each body, then the volume of a sphere with radius $r_{cutoff}$ could be substituted for $V_{interaction}$. This would be the case for a system as the number of bins goes to infinity, and the volume of the bins goes to zero, in the limit of the system. In the three dimensional case, where $V_{interaction}$ is the volume of a sphere with the radii $r_{cutoff}$ we can substitute the equation for the volume of a sphere for $V_{interaction}$ to yield the equation:

$$\text{Ideal Scaling} = \frac{N^2 \cdot \frac{4}{3} \cdot \pi \cdot r_{cutoff}^3}{l_x^{system} \cdot l_y^{system} \cdot l_z^{system}} \quad (12)$$

This ideal situation, however, is impossible to achieve because it requires an infinite number of bins. However, that serves as the lower bound achievable through the use of the binning technology. But we can also approximate the upper bound that is achievable with the cubic approximation system by substituting the $V_{interaction}$ term with the $V_{r_{cutoff}}^{cubic}$ term. Although this assumes an even distribution of the N bodies in the bins, it is a reasonable approximation for many molecular simulations. This substitution gives the scaling behavior as:

$$\text{Scaling} \propto \frac{N^2 \cdot M_{bins} \cdot V_{bins}}{l_x^{system} \cdot l_y^{system} \cdot l_z^{system}} \quad (13)$$

Substituting the equation for the volume of a cubic bin, from equation (8) and recalling from (2) that $o = l^{system}/l^{bin}$, we obtain a bounding of the efficiency of the device as:

$$\text{Scaling} \propto \frac{N^2 \cdot M_{bins}}{o_x \cdot o_y \cdot o_z} \quad (14)$$

By applying the equation for calculating the number of bins in the cubic approximation, $M=(2k+1)$ for each of the three dimensions, we can obtain $$\text{Scaling} \propto \frac{N^2 \cdot (2 \cdot k_x + 1) \cdot (2 \cdot k_y + 1) \cdot (2 \cdot k_z + 1)}{o_x \cdot o_y \cdot o_z} \quad (15)$$

By writing the equation in vector notation, we obtain $$\text{Scaling} \propto N^2 \cdot \prod_{i=x,y,z\ldots} \frac{2 \cdot k_i + 1}{o_i} \quad (16)$$

which can also be written, by substituting back equation (3), as $$\text{Scaling} \propto N^2 \cdot \prod_{i=x,y,z\ldots} \frac{2 \cdot \text{ceil}(r_{cutoff} \cdot o_i / l_i) + 1}{o_i} \quad (17)$$

This equation can be applied with rectangular bins, and to any positive number of dimensions, given by i.

Binning Approximations

The following demonstrates two methods that can be used to approximate the area or volume covered by the $r_{cutoff}$ parameter in a binned system. In the first and most simplified method, a cube of bins is used, in which a cube of bins is created using 2k+1 bins in each dimension centered on the bin from which the $r_{cutoff}$ radiates. This method is simple to set up, but has the overhead of included bins containing only bodies that are definitely beyond the $r_{cutoff}$ radius. This only typically becomes an issue for systems where the k parameter is larger than 3.

The second method is to use a spherical approximation, in which any bin with a closest point distance to the center bin is greater than the distance of $r_{cutoff}$ is eliminated from the list of searched bins. Aside from the minimal complexity and time required to check each of these minimum distances between bins, there are some advantages to using this method. This becomes even more so when a relative bin map is used, allowing this operation to be done once upon initialization of the binning system, and stored in the bin map, thus reducing the overhead of the method and the computational time required by iterating over the empty bins. However, it can be difficult to find an equation based on the system variables (o, $l^{system}$ and $r_{cutoff}$) that describes the number of bins removed using this method, making it difficult to predict the exact scaling of this method. However, the scaling behavior follows the same trends as the cubic binning, simply multiplied by a constant that tends towards $\pi/6$, the ratio of the volume of a sphere to a cube.

In the spherical approximation, the bins are still in the shape of cubes (or near-cubic rectangular prisms). The ability to approximate the volume of a sphere built from cubes becomes more accurate as the size of the cubes relative to the size of the sphere (with radius $r_{cutoff}$) become smaller. When non cubic system sizes are used, it may be difficult to generate bins that have identical side lengths, given the constraint that the number of bins along each edge, o, can be a whole number (e.g. an integer), a constraint condition for systems using periodic boundary conditions. Thus, binning may also be done with non-cubic bins, becoming advantageous for larger systems with higher binning orders.

For higher values of k, the cubic approximation of $r_{cutoff}$ becomes worse compared to the spherical approximation and, for large values of k, can cause the system to iterate over 170% of the volume covered by the spherical approximation map.

Figure 4:
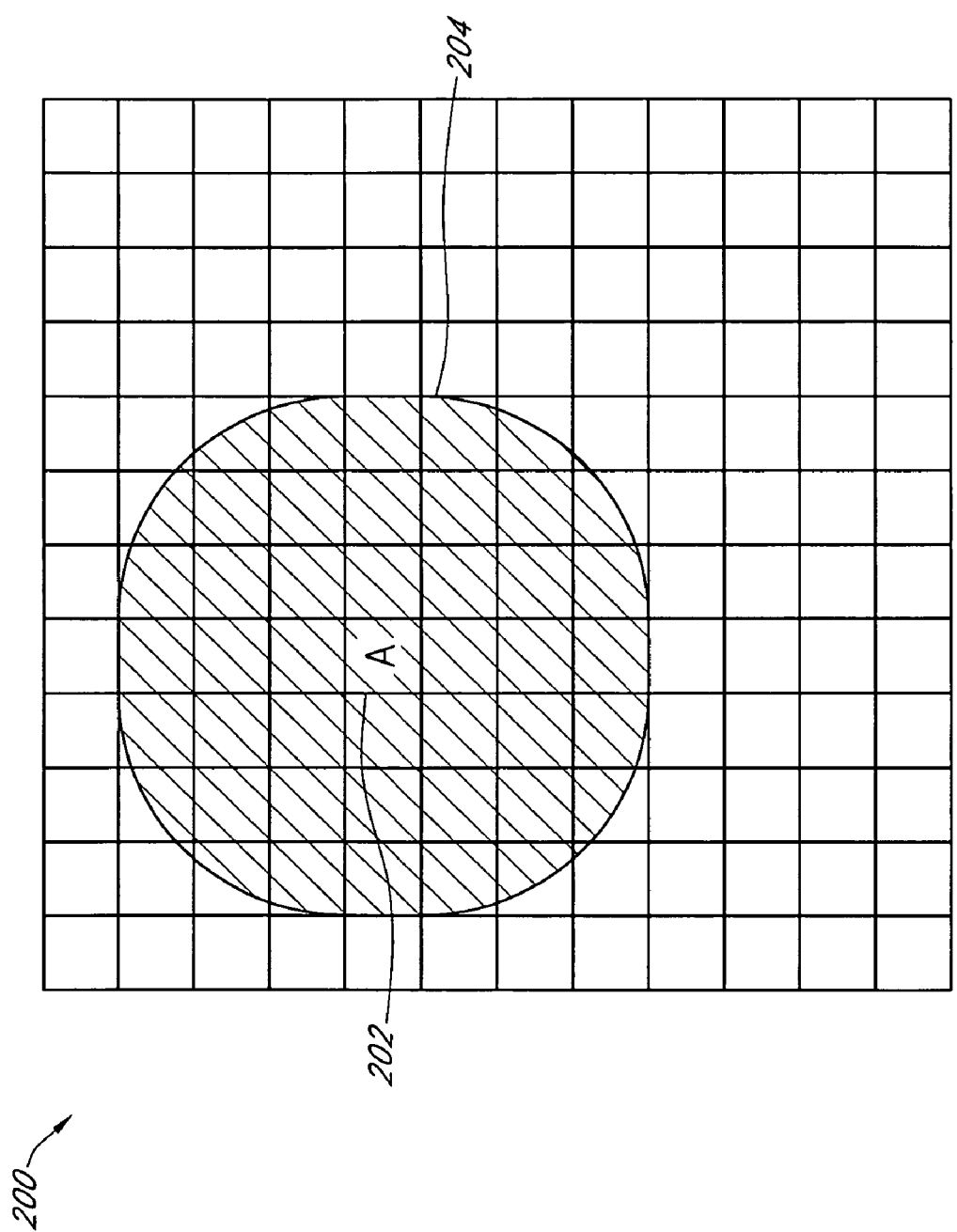
FIG. 4 illustrates how a cutoff approximates a circle as values of k increase.

In FIG. 4, the cell A 202, and the area 204 that falls within the distance of $r_{cutoff}$ is shown by the round shape encircling it at a distance of 3 times the cutoff. This illustrates a system where the $r_{cutoff}$ parameter is three times the length of the edge of a bin ($l^{bin}$) and requires a depth of three bins along each axis to include all of the cells. As mentioned previously with regard to equations (1)-(3), $r_{cutoff}$ can also be written as the vector k, which describes set of k parameters in each dimension. Because of the relationship between $l^{bin}$, and the order and length of the system itself, the value of k can also be calculated from the system parameters. k always describes the depth in the number of bins between the center cell and the distance $r_{cutoff}$ in each dimension. The ceil function is required to include entire bins, when any part of the bin falls within the $r_{cutoff}$ radius from the center bin.

FIG. 4 illustrates how a cutoff approximates a circle as values of k increase within a simulation space 200. As the k value increases, the square with rounded corners becomes more circular shaped. As with FIG. 3, the area 204 within the rounded square describes the area in which bodies outside of bin A 202 might be interacting within a body within the bin A 202. As noted above, the entire contents of a bin overlapped by any portion of the area 204 are included as if the bin was completely encompassed by the area 204 within the $r_{cutoff}$ distance from bin A 202.

Figure 5:
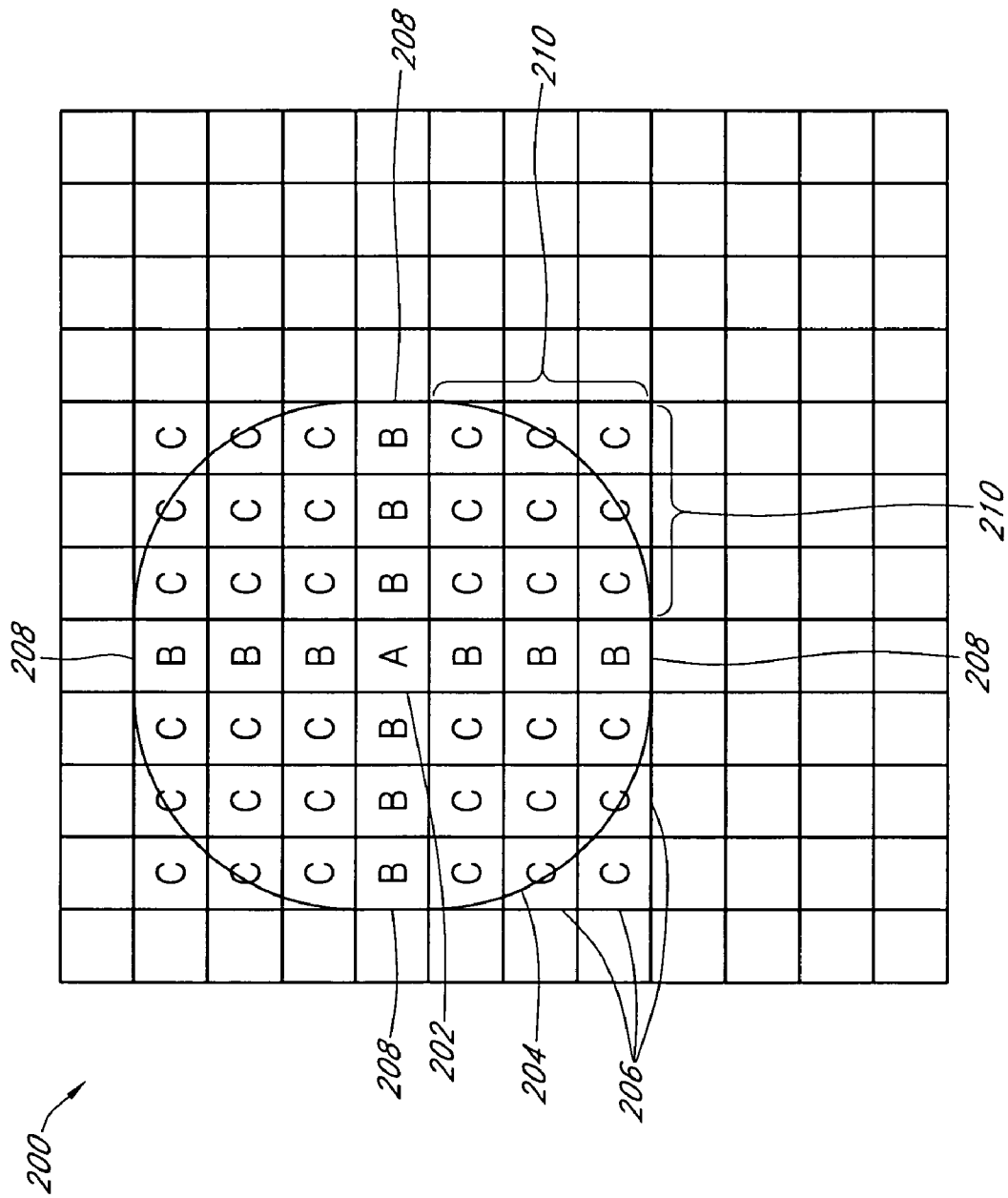
FIG. 5 illustrates a two dimensional cubic approximation with a k value of 3.

FIG. 5 illustrates a two dimensional cubic simulation space 200 with a k value of 3. In the two dimensional cubic approximation binning system there are $(2k+1)^2$ bins. Thus, the number of bins is given by the expansion $1+4k+4k^2$. The 1 bin (bin A 202) is found at the center. The 4k bins 208 radially extend from the center bin (each bin marked "B"). The $4k^2$ bins 210 fill out each corner (each bin marked "C") within the $r_{cutoff}$ radius. The whole of the area 204 is shown as a near circular shape. A similar pattern is seen in for three dimensional binning systems with the equation $(2k+1)^3$. This pattern will be discussed further with reference to FIG. 6. As with the bins in FIGS. 2, 3 and 4, the area 204 within the rounded square describes the area in which bodies outside of bin A 202 might be interacting within a body within the bin A 202. Further, the entire contents of a bin overlapped by any portion of the area 204 are included as if the bin was completely encompassed by the area 204 within the $r_{cutoff}$ distance from bin A 202.

Figure 6:
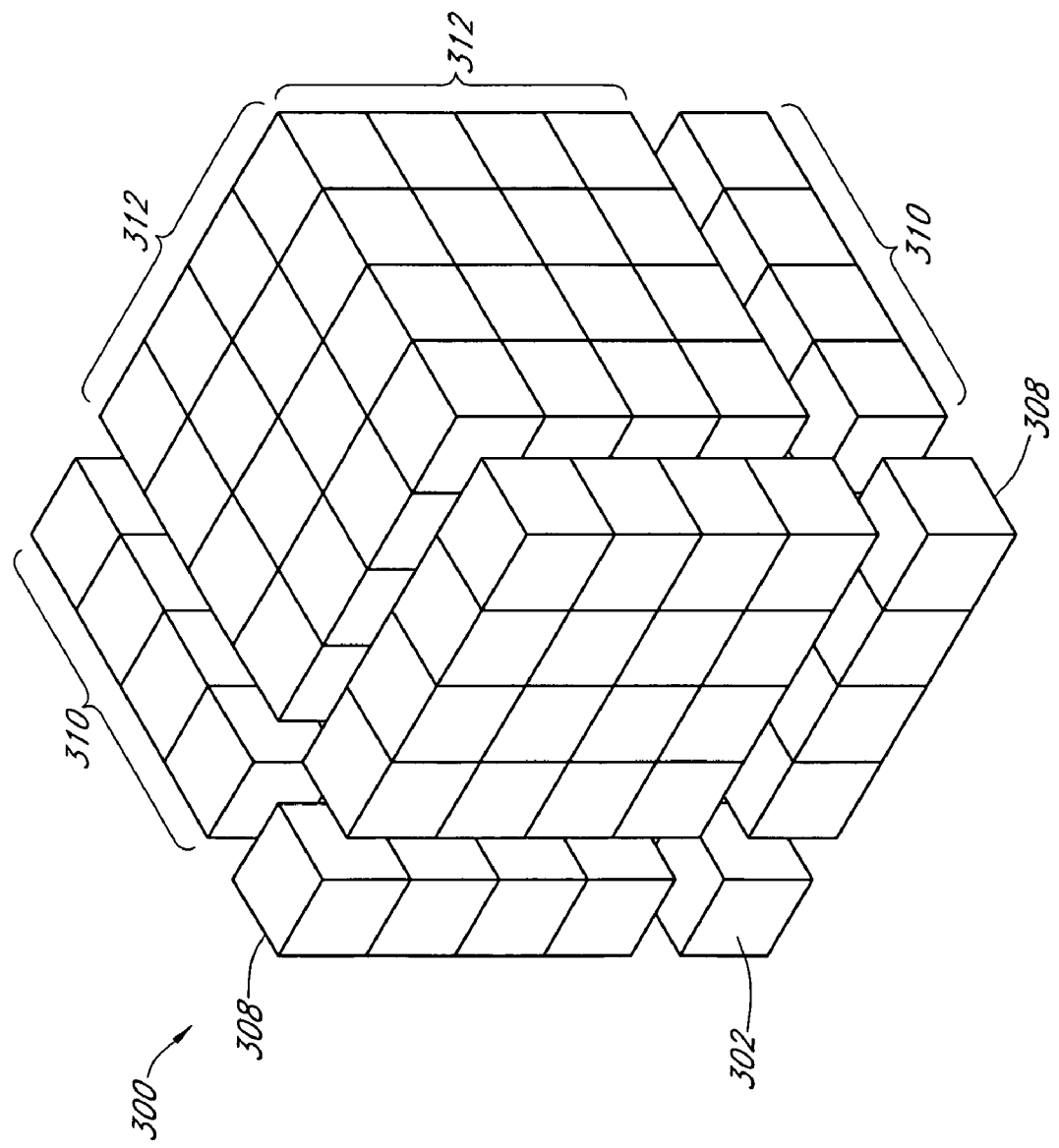
FIG. 6 illustrates a portion of a three dimensional cubic approximation binning system.

FIG. 6 illustrates a cut away portion of a three dimensional cubic approximation of the bins within a bin map 300. The bin map 300 is the list of bins which may contain interacting bodies for any given bin as a starting point—with k=4. The bin map 300 illustrates the expansion of the $(2k+1)^3$ to $1+6k+12k^2+8k^3$. As in the two dimensional system, the three dimensional bin map 300 includes a cubic center bin 302. Extending radially from the center bin 302 are two sets of 6k bins 308. Filling out the second dimension are three of the 12 sets of $k^2$ bins 310. Filling out the third dimension is one of the 8 corner groups of $k^3$ bins 312.

In the embodiment of FIG. 6, the illustrated bin map has bins that are the same length in each dimension. However, it should be realized that the method does not require that bins be the same length in each direction. For example, in a system in which x ◇y ◇z, the same equation is left in the expanded form, each term contains unique directional terms. In this case, it can be shown that each of the groups of bins, in fact, has a specific term:

$$M_{bin}=1+2k_x+2k_y+2k_z+4k_xk_y+4k_yk_z+4k_yk_z+8k_xk_yk_z \quad (18)$$

A system where spherical approximation binning (see below) is used, the $8k_xk_yk_z$ term is replaced with a function describing the number of bins—no equation is currently known that describes this series. However, $M_{bin}$ can be determined empirically. An illustration is provided for the two dimensional case, for a system with k=8 in both dimensions.

Figure 7:
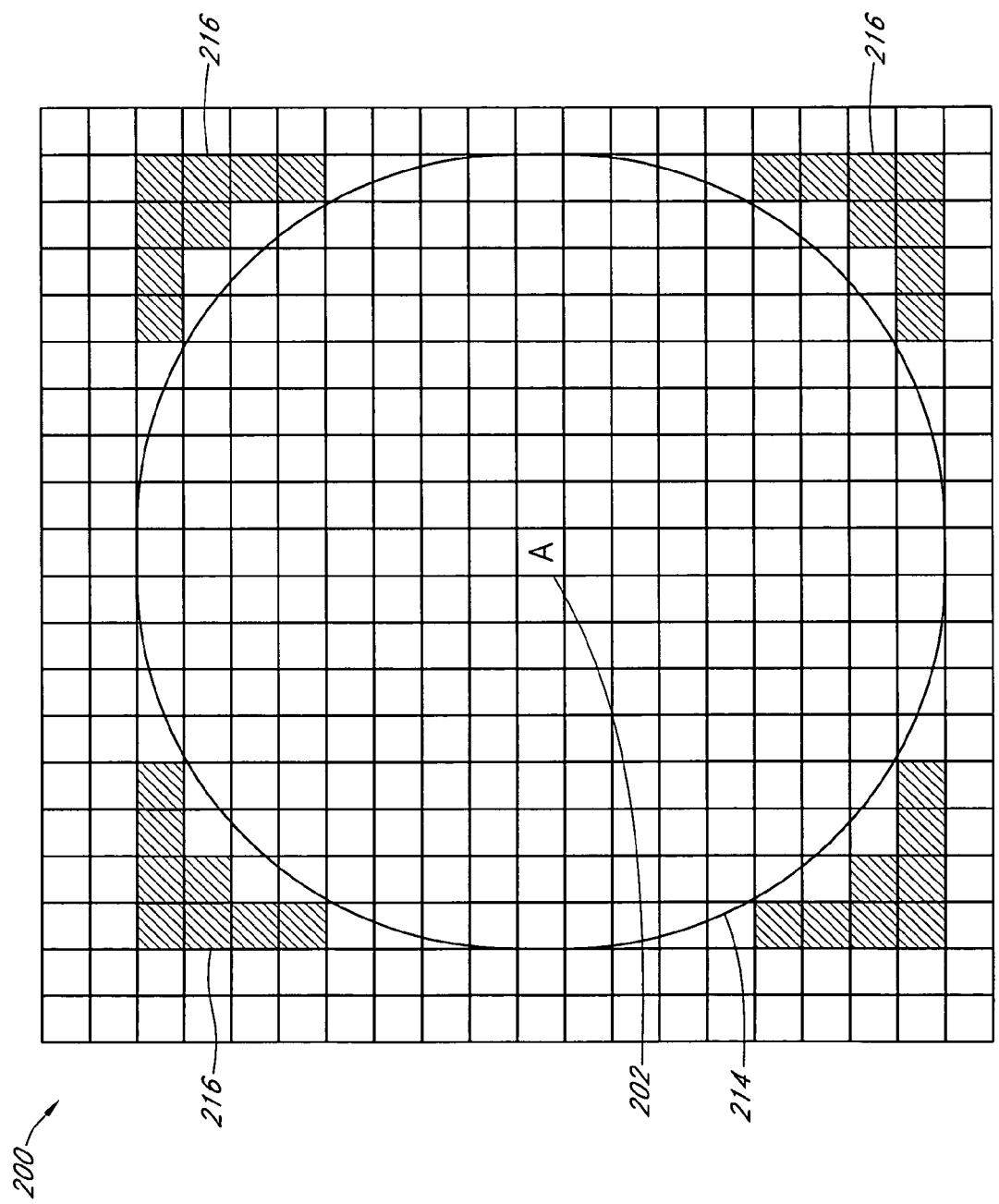
FIG. 7 illustrates a two dimensional representation of a spherical approximation binning system, with a k value of 8.

FIG. 7 shows the difference in bins that would be included in the cubic approximation, but would be excluded in the spherical (or circular) approximation.

FIG. 7 illustrates a two dimensional representation of a spherical approximation binning system 200, with a k value of 8. All bins that fall within the distance of $r_{cutoff}$ of the center bin A 202, are included in a spherical binning approximation binning map 214. The shaded bins 216 would not be included in the spherical approximation binning map 214. In contrast, shaded bins 216 would be included in cubic approximation binning maps. In this example, the difference in cell totals is 32 bins. (This effect is much more dramatic in three dimensions.) As the k value increases, the area included by cubes approximating the area defined by $r_{cutoff}$ begins to appear more circular, and much less like a square with rounded corners. Thus, as the value of k increases, the difference between the cubic approximation and the spherical approximation also increases.

Bin Mapping

In order to identify bins internally, each bin is given a unique numeric identifier. This allows each bin to be queried by the integrator as required, and to facilitate placing bodies into, and retrieving bodies from a bin. The location of a bin within the system, and the unique bin number should be immediately determinable from its coordinates, which also enables the creation of a map specifically to indicate which bins can be iterated over for determining interactions for a body in a selected bin. The numbering itself does not require a separate map, but allows the relevant bin identifier to be determined on the fly from a body's coordinates, or from interpreting the relative bin map from a given position.

Figure 8:
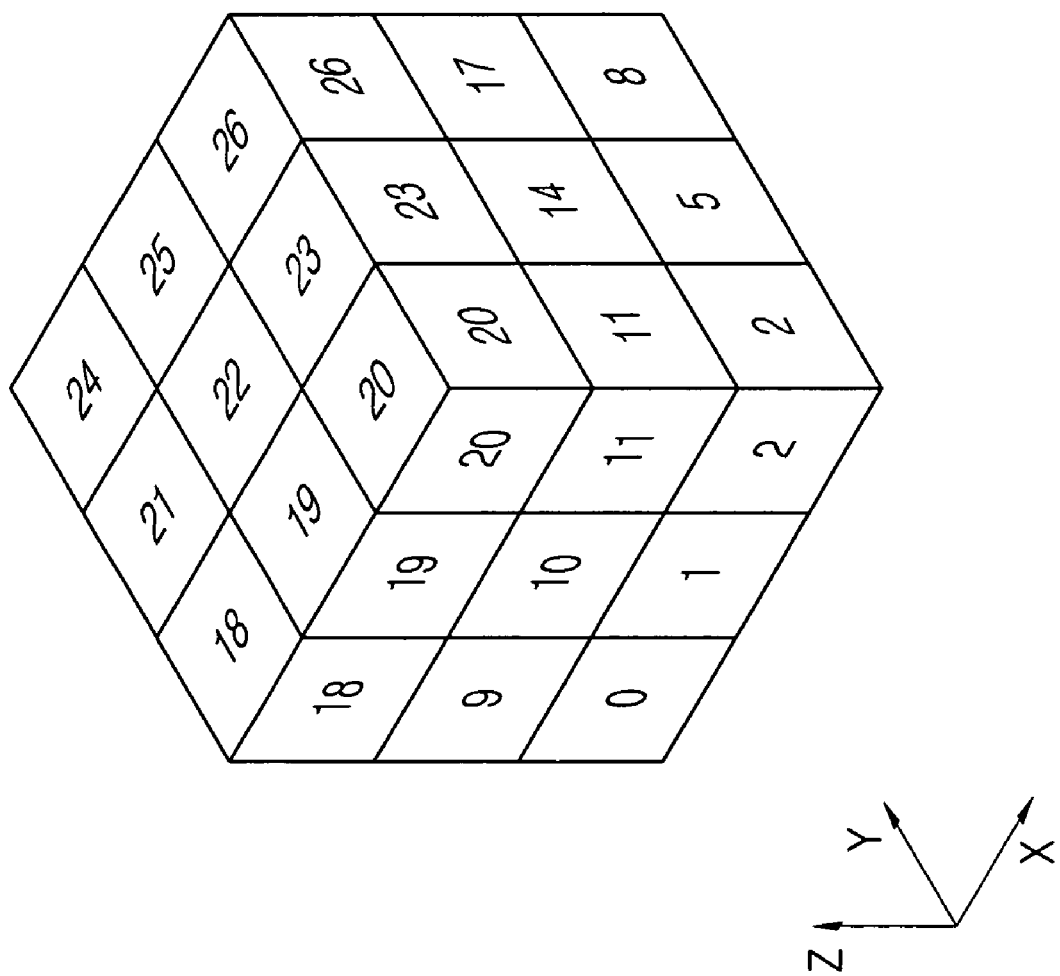
FIG. 8 illustrates a binning system with an order of three in each dimension.

The unique numbers for each bin may be assigned by a simple numbering scheme, starting at one corner, and proceeding in a row, column and then depth wise manner, assigning consecutive integers until each bin has been assigned an identifier. This method is used to assign identifiers to the bins. FIG. 8 illustrates a binned system with unique numbers assigned to each bin. The binning system has an order (o) of three in each dimension (a 3×3×3 cube). Bins are numbered from zero, starting from the bin at the origin, and proceeding first across the x dimension to fill each row. After a single row is filled, the next row in the y dimension is numbered, in the same direction as the last. When the last row in the y dimension is numbered, the same numbering scheme is continued in the next plane in the z dimension. As illustrated in FIG. 8, bins are numbered consecutively down the first axis (for example, [0,1,2]), numbered in intervals of the order in the first dimension in the second axis (for example, [2,5,8]), and numbered in intervals of the product of the orders of the first two dimensions in the third (for example, [0,9,18]).

In one embodiment, locating which bin contains a particular point in space uses the coordinates of the point with respect to the origin of the system. This method requires that all bodies within the binned system exists within the space defined between the origin and the length of the system in each dimension (e.g., the binned bodies can have coordinates in each dimension that are bounded by zero and $l^{system}$). For bodies which are not binned, which is the case for non-parent bodies (discussed further below with regard to group based cut-offs) this restriction does not hold. When using periodic boundaries, however bodies may exist outside of this space by being "wrapped around" the system boundaries to be placed in the corresponding bin.

Moving the other direction, determining which bodies are near by from a particular bin, can be done with a bin map. The bin map is a list of all neighboring bins which border any given bin, and may have bodies that are within the area swept out by $r_{cutoff}$.

For systems using the cubic approximation method, the map will contain $(2k+1)^D$ bins, where D is the number of dimensions in the system. For systems using the spherical approximation, the number of bins given by the $(2k+1)^D$ equation provides an upper bound on the number of bins included, however, as k increases, the spherical approximation will tend towards using only 60% of the number of bins used in the cubic approximation. No equation is currently known that can identify the number of bins used in the spherical approximation based solely on the system parameters, however, it can be determined empirically with very little effort. Table 1 shows the values for k from 1 to 24.

TABLE 1

| k  | bins (cubic) | bins (spherical) |
|----|--------------|------------------|
| 1  | 1            | 1                |
| 2  | 8            | 8                |
| 3  | 27           | 23               |
| 4  | 64           | 51               |
| 5  | 125          | 90               |
| 6  | 216          | 157              |
| 7  | 343          | 230              |
| 8  | 512          | 341              |
| 9  | 729          | 471              |
| 10 | 1000         | 639              |
| 11 | 1331         | 835              |
| 12 | 1728         | 1063             |
| 13 | 2197         | 1340             |
| 14 | 2744         | 1671             |
| 15 | 3375         | 2022             |
| 16 | 4096         | 2443             |
| 17 | 4913         | 2893             |
| 18 | 5832         | 3428             |
| 19 | 6859         | 4004             |
| 20 | 8000         | 4653             |
| 21 | 9261         | 5359             |
| 22 | 10648        | 6133             |
| 23 | 12167        | 6977             |
| 24 | 13824        | 7907             |

Bin Maps Forms and Memory Usage

A significant trade off, in terms of processing power vs. memory, can be found during the creation and use of the map of all neighboring bins within the cutoff distance, $r_{cutoff}$, from any point in the system. In some embodiments, in order to iterate over all of the possible bodies that may be interacting with a selected body, the iterator can know in which bins check for them. This can be done by providing the iterator a map to guide the process. There are two possible types of map, one of which may be calculated on the fly, the other is processed beforehand, providing each bin with a complete map of it's neighbors. Combinations of these two types of maps may be used as well.

In the first type, a pre-processed map, each bin stores a unique identifier for each of the neighboring bins that fall within the distance $r_{cutoff}$ from any edge of the current bin. This map is then be stored for each bin. Storing this map requires a significant amount of memory, however there is almost no overhead for the iterator to determine the next bin when iterating over the whole list of possible interacting bodies. The amount of memory taken up by this approach is [sizeof(int)*$(2k+1)^3$*$o_x$*$o_y$*$o_z$], k being the depth of the bins in which it can look, and $o_x$, $o_y$, and $o_z$ are the number of bins along each edge, with their product yielding the number of bins in the system.

For a map calculated in real time, there is no memory requirement for the storage of the map, however, in some embodiments the same map can be re-calculated each time the neighbors of a bin are to be iterated over. Thus, it takes significant computational time to locate each bin on each iteration. It's possible that some of the advantage of using the binning method would be lost by performing this operation, which would also require $N \cdot o^3$ operations to complete. Although still smaller than $N^2$ time, This is a significant overhead compared to having the map pre-computed.

Figure 9:
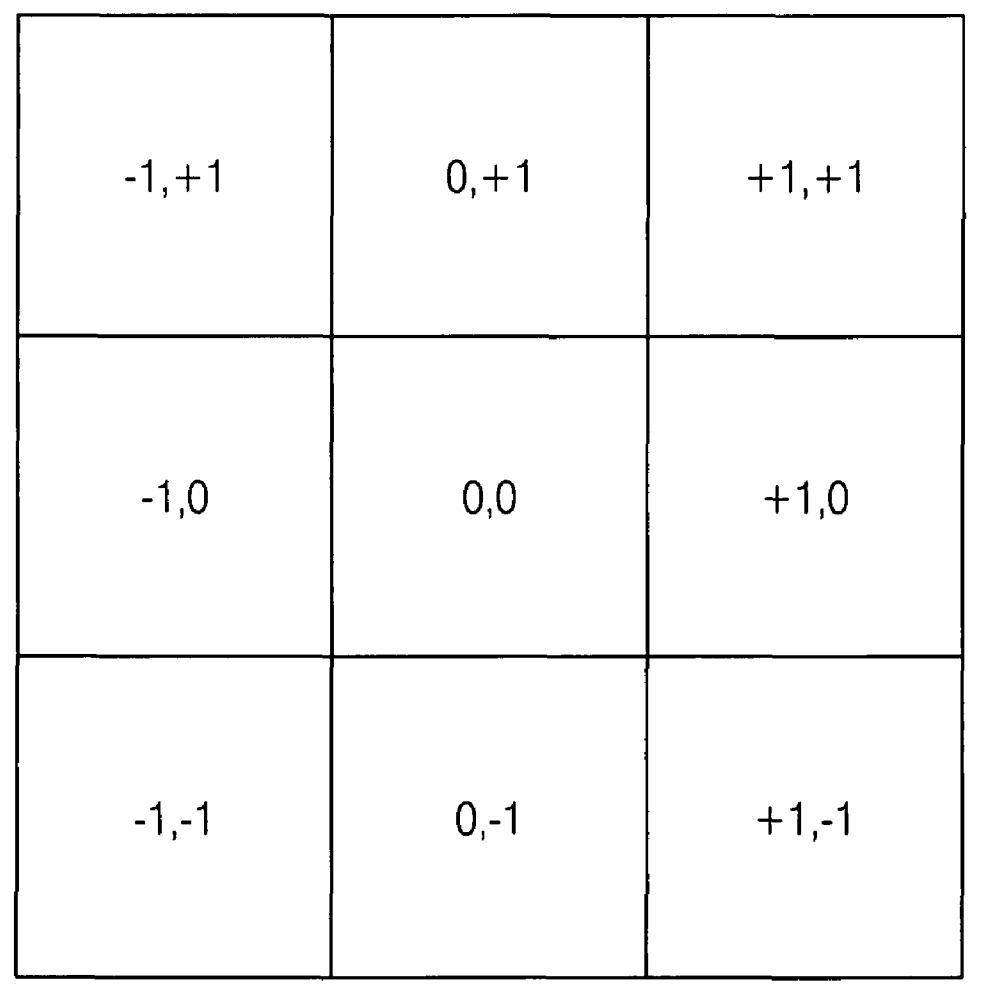

The third type, a hybrid method of the other two, uses a relative map that can be applied to any cell. In some embodiments this method stores only one map, which keeps the relative positions of all of the neighbor bins over which the iterator may pass. FIG. 9 illustrates a relational map for the center cell in a 3×3 group of cubes. The relational map itself can be wrapped around the edge of the system, allowing periodic boundaries to be used. The first number in each bin is the shift in the horizontal direction, whereas the second number is the shift in the vertical distance. The amount of processing required to convert this map into absolute bin number identifiers for each bin is small, and more than compensates for the reduced amount of memory required for systems with large values of k, and the amount of memory required becomes independent of o.

This relational map stores the minimum required information for locating all of the neighbor bins, takes up relatively small amounts of memory. (for example, the worst case, using cubic binning in three dimensions requires $(2k+1)^3$ times the size of an integer) With this scheme, maps for cubical approximation binning with values of k up to 30 can be done with less than 1 Megabyte of memory, and a k value of 67 can be done with less than 10 MB. For systems with large values for k, memory usage can be further reduced by using spherical approximation binning, in which the binning maps memory requirements are reduced to 55-65% of the size required by the cubical approximation.

FIG. 9 illustrates a relative bin map. Relative maps can be used in two senses in binning. In the first sense, it can be used to show the relative positions of two bins. In the second, a similar relative system can be used to keep track of bodies that wrap in and out of the binned systems.

Interface

The binning method can be fitted with a number of different interfaces that allow the information in the bins to be retrieved. In a preferred method, a system of iterators is used. An iterator greatly simplifies the required operations that need to be implemented by the user of the interface. Thus, the binning method presents a limited set of functions to a user or other device. The functions available can be broadly grouped into four sets: Setup functions, Cleanup functions, Iterator functions and functions for moving bodies between bins.

Functions accessible to the user or agent:

Initialization:

```
bin_manager_t *bin_init (const system_t *sys,
    const Vectori *in_order);
void bin_do_bin_system (const bin_manager_t *bm,
    const system_t *sys, const bin_set_t *set);
```

Iterator controls:

```
void bin_fill_list_iter_next (bin_list_iter_t *it);
char bin_fill_list_iter_end (bin_list_iter_t *it);
void bin_fill_list_iter_begin (bin_list_iter_t *it, bin_fill_node_t
        *start_node);
void bin_fill_list_iter_cur (const bin_list_iter_t *it, int *mol,
        int *atom, Vectorc *wrap);
void bin_iter_begin (const bin_manager_t *bm, const bin_set_t
        *set,int cell, bin_iter_t *it, int bound);
void bin_iter_next (const bin_manager_t *bm, const bin_set_t *set,
        bin_iter_t *it);
void bin_iter_get_cur (const bin_iter_t *it, int *mol, int *atom,
        Vectorc *wrap, Vectorc *shiftvector);
char bin_iter_end (bin_iter_t *it);
``` moving between cells:

```
int bin_cell_ijk2idx_wrap (const bin_manager_t *bm,body_t
        *atom,const Vector *system_width, Vectorc *wrap);
void bin_atom_bin_check (const bin_manager_t *bm, const system_t
        *sys, bin_set_t *set,int mol, int *parent_atom_cell);
```

Binning optimizer:

```
void bin_optimizer (Vectori *bin_order, const int MAX_ORDER,
const int num_bodies, const int
        num_parent_atoms, const float switch_max,
        const Vector *system_width);
```

Miscellaneous (used by barostat):

```
void bin_calc_cell_width (Vectord *cell_width,
        const Vector *system_width, const Vectori *order);
```

Clean-up:
    void bin_deinit (bin_manager_t *bm);

Cleanup

Once the user or agent is done with the binning method, the device can be closed in two ways, performing either a reset back to it's initial state, or a termination operation.

Resetting the binning method can be done to different depths, depending on the further use of the bins. In the case where the bins are to be reused, simply erasing the contents of the bins may be sufficient. This can be done by overwriting the values stored in locations of the memory holding the binning information, and resetting the variables in each bin, or in the case where the bins are a simple linked list of atoms, by clearing the head node of the linked list. Code for this function is given in Appendix B in the function bin_clear_bins( ).

The binning method may be terminated, or turned off, in which case all memory used by the binning method should be de-allocated. Because restarting the binning method is a relatively quick process, it is often advantageous to simply terminate the binning method's operation, and simply restart it with the parameters used by the next system to be binned. Code for this function is given in Appendix B in the function bin_deinit( ).

Iterator

The iterator method is particularly advantageous for use with a binning method, as it allows the device to operate independently of the simulation systems or other agent for which it performs the binning function.

A second advantage exists because of the iterator's ability to hide a significant portion of the operations of the binning method from the agent systems, that are ideally not required to understand or interface with the binning method's core routines. However, this can proceed through different levels of abstraction. In the interface described above, iterators are provided for both the bin map and the fill list. This provides a significant level of control for the agent accessing the binning method. Full code is provided in Appendix B, in the functions whose names begin with bin_iter and bin_fill_list_iter.

For other applications, a simpler interface can be provided, where the only iterator functions provided to the user are the functions to:
    1. Reset the iterator to the start of the binmap/fill list.
    2. Move to the next map element or body in the fill list, and indicate the end.
    3. Return the body at the current position in the iterator.

In this interface, the iterator automatically handles moving to the next bin and is required to return an end of iterator character, to indicate to the user or agent once the end of a fill list is reached. This could be provided by wrappers around the bin_fill_list_iter and bin_iter functions provided in Appendix B.

Figure 10:
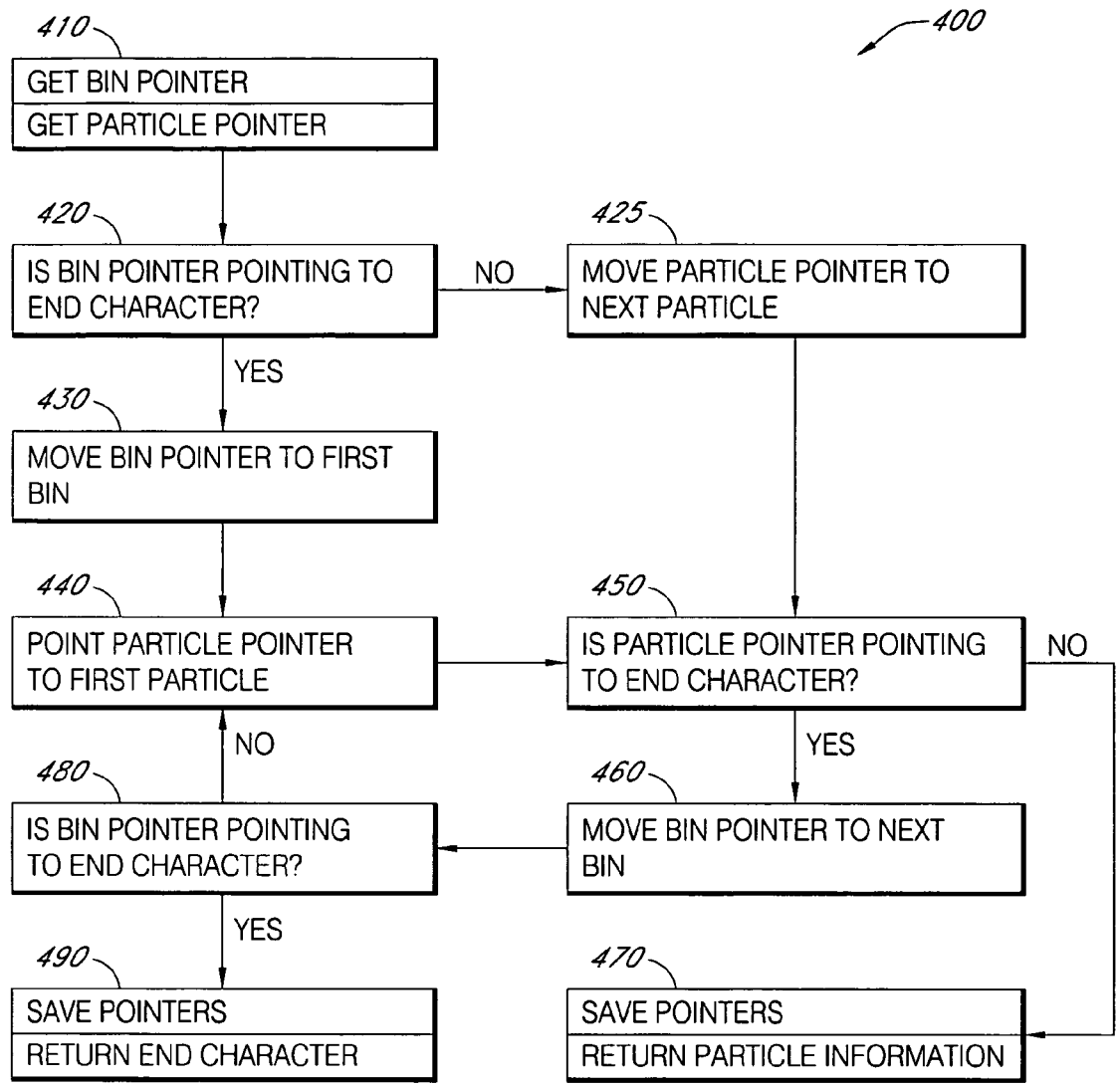
FIG. 10 illustrates a state diagram for the iterator interface of the binning method.

This process can be described in a process 400, as shown in FIG. 10. In step 410 the system gets a bin pointer and a particle pointer. In step 420 the system asks whether the bin pointer is pointing to an end character. If it is, the system moves to step 430, moves the bin pointer to a first bin and then moves to step 440, points the particle pointer to a first particle and then moves to decision state 450. If the bin pointer is not pointing to an end character, the system moves to step 425, moves the particle pointer to the next particle and then the system moves to decision state 450. In decision state 450, the system asks if the particle pointer is pointing to an end character. If it is not, the system moves to step 470, the system saves pointers and returns particle information. If it is, then the system moves to step 460, moves the bin pointer to the next bin, and the system moves to decision state 480. In decision state 480 the system asks if the bin pointer is pointing to an end character. If it is, the system moves to step 490, saves pointers and returns the end character. If it is not, the system returns to step 440. Once the binning method as been initialized and the bodies have been placed in to their assigned bins, the binning method can be used. At any point, the user or an agent can query the device for the next body, and the binning method will follow the pathway shown.

Binning Bodies

The process of putting a body into a bin is computationally straightforward. The information about the body itself is not moved, as the binning system itself does not store the actual body, but simply the meta information about where to find the body. As bodies can be stored in various arrays, the binning can store simply the array index for the location of the body. Two circumstances exist, however, for storing bodies into a bin. The first is for binning (or re-binning) an entire simulation, and the second is for transferring a single body from one bin to another. The code for binning the entire system can be found Appendix B as the function bin_do_bin_system( ), and can be called by the user or agent. The code for re-binning an atom is not directly user accessible, however, a function is provided for the user to check if the bin has changed, and if it has, to re-bin the atom. This code is found in Appendix B in the function bin_atom_bin_check( ), which calls the private function bin_do_rebin_atom( ).

Binning with Parent Bodies (Group Based Cut-Offs)

The binning method is compatible with many commonly used features of molecular simulations, including group based cutoffs and switching functions. By creating groups of bodies in which only one distance is compared for the group of bodies, it is possible to reduce the need to compare distances between every individual set of bodies within neighboring bins. In each group, one body is designated as the "parent" of the group, which allows for a single distance to be sampled for each body within the group. The switching function allows for groups to interact with each other near the cutoff radius, without introducing sudden jumps in interaction energies. For implementation details and further discussion on group based cutoffs. See Steinbach and Brooks, *New Spherical-Cutoff Methods for Long-Range Forces in Macromolecular Simulation, Journal of Computational Chemistry*, 15:667-683 (1994), which is hereby incorporated by reference in its entirety.

Bins of Other Shapes

Although embodiments of the invention utilize bins that are cubical, the invention is not so limited. Other non-cubic shape bins, such as rectangular bins can provide improvements in system performance. These alternatively shaped bins also enable the study of systems with non cubic dimensions. Further, they remove the requirement that both the bin dimensions and all three system dimensions share a lowest common denominator value.

The binning method explained herein may also be expanded to use other shapes than cubes or rectangular prisms for the bins themselves. Any shape that can be tiled in the required number of dimensions without leaving gaps can be used. For two dimensional systems, triangles, hexagons and irregular pentagons are some of the shapes that can be used. Similarly, in three dimensional systems non-cubic shapes may be used including any body that may be tiled. Examples of other three dimensional shapes include prisms, three dimensional trapezoids, dodecahedrons and octahedrals. It is worth noting that the goal of selecting different shapes is to create a better approximation of the volume inside of the $r_{cutoff}$ distance from any edge of the center tile.

Boundary Conditions

The binning method is compatible with commonly used boundary conditions. In the case where the system size is not maintained as a constant, the system size can either be expanded to include bodies that drift away, or the system size used in the binning can be large enough to encompass the simulation at it's widest point of a fixed length simulation, both of which are trivial cases for the use of the binning method. For more discussion of boundary conditions, see Leach, supra.

Binning Optimization

One embodiment of the invention uses an enhanced method embodied in a binning optimizer to optimize the number of bins in order to increase the computational efficiency of the system. Knowing the number of bodies, the cutoff radius ($r_{cutoff}$) and the system size ($l_{system}$), it is possible to determine the most optimal number of bins into which the system should be divided. Essentially, this can be done by solving equation (17) for the lowest value, disregarding solutions in which the average number of bodies per bin is less than 1. Because the scaling behavior of spherical approximation binning is a scaled version of the cubic approximation, equation (17) can be used for optimizing both methods. The source code for the binning optimization function is given in Appendix B, and uses a simple implementation of the binning optimization algorithm.

Another binning method relates to increasing the number of bins until it becomes impossible for two bodies to be placed in a single bin. This method has the advantage that the bins themselves require less structure, which also enables the program to simply ask "is the bin occupied, or not." See Allen and Tildesley, *Computer Simulation of Liquids*, Oxford University Press, Oxford, p. 151 (1987), which is hereby incorporated by reference in its entirety. However, one drawback of this method is that it requires an overstatement of the number of bins required to meet the condition of no more than one body per bin. Thus, this method utilizes significantly more checks of whether bins are occupied than would otherwise be necessary.

Parallelization

One of the advantages of using the above described binning methods is the easy expansion to parallel computational systems. Because the binning method has decomposed the system based on spatial divisions, the application and expansion to a parallel computational system becomes relatively simple. The most elementary method is to use parallel iterators within the binning method, which allows coordination between other devices. An alternative method is to allow each node to maintain an iterator, and simply divide the system between processors. Both methods allow multiple agents to work within different portions of the system in parallel. This device can also be used with any other variation of the Domain Decomposition algorithms, see Plimpton, S., 1995, *Fast Parallel Algorithms for Short-Range Molecular Dynamics, J. Comput. Phys.* 117:1-19, which is hereby incorporated by reference.

A Framework for Decomposing N-body Problems for Rapid Parallelization

Parallelization is the process by which a single computational task can be broken down and spread over multiple computers. Using the binning method in combination with software able to apply the domain decomposition algorithms allows for a relatively rapid parallelization effort. Although many variants of domain decomposition exist, all should be compatible with the binning method.

EXAMPLES

The binning method described above has been implemented as a module of a "ZymeCAD Molecular modeling application". Appendices A through C provide source code showing illustrative embodiments of the methods of the instant application.

Results and Testing

The binning method was implemented as described, and tested to ensure that performance exists as described. Because of the emphasis on optimization of the binning method, two particular tests are used to demonstrate that the optimization functions as predicted. The first is the ability to predict the optimized behavior for large and small systems as a function of the selected order (o parameter), which allows for the optimal number of bins to be used. The second is the speed of the binning method, which maintains an O(N) performance—depending on the number of bodies in the simulation, rather than the number of bodies, squared.

Scaling as a Function of Order

The system used to test the scaling as a function of order was done with the following parameters:

l=[62.128 Å, 62.128 Å, 62.128 Å]
r=15 Å
N=24,000 bodies

Values for o, identical in each dimension ($o_x=o_y=o_z$), were provided in increments of one, from 1 to 20, and for the values 22, 25, 27, 30, and 35. The 24,000 bodies were composed of 8000 TIP3P water molecules, where only one atom per molecule was binned, using a group based cut off. For each supplied set of orders, one hundred Monte Carlo steps at 298K were attempted, where each step involves either a center of mass rotation or a translation of each water molecule, using a 30% acceptance ration for both move types. Boundary conditions for the simulation were periodic, allowing molecules to wrap around each edge into the other side of the box. For comparison, a simulation was completed using the $N^2$ algorithm, in which binning is turned off. The CPU time required to complete each simulation was measured.

All simulations were performed with v. 3332 of ZymeCAD and compiled with full optimization using the gcc compiler. The processor used for these simulations was a 2.2 GHz AMD Athlon 64 with a cache size of 512 KB.

Figure 11A:
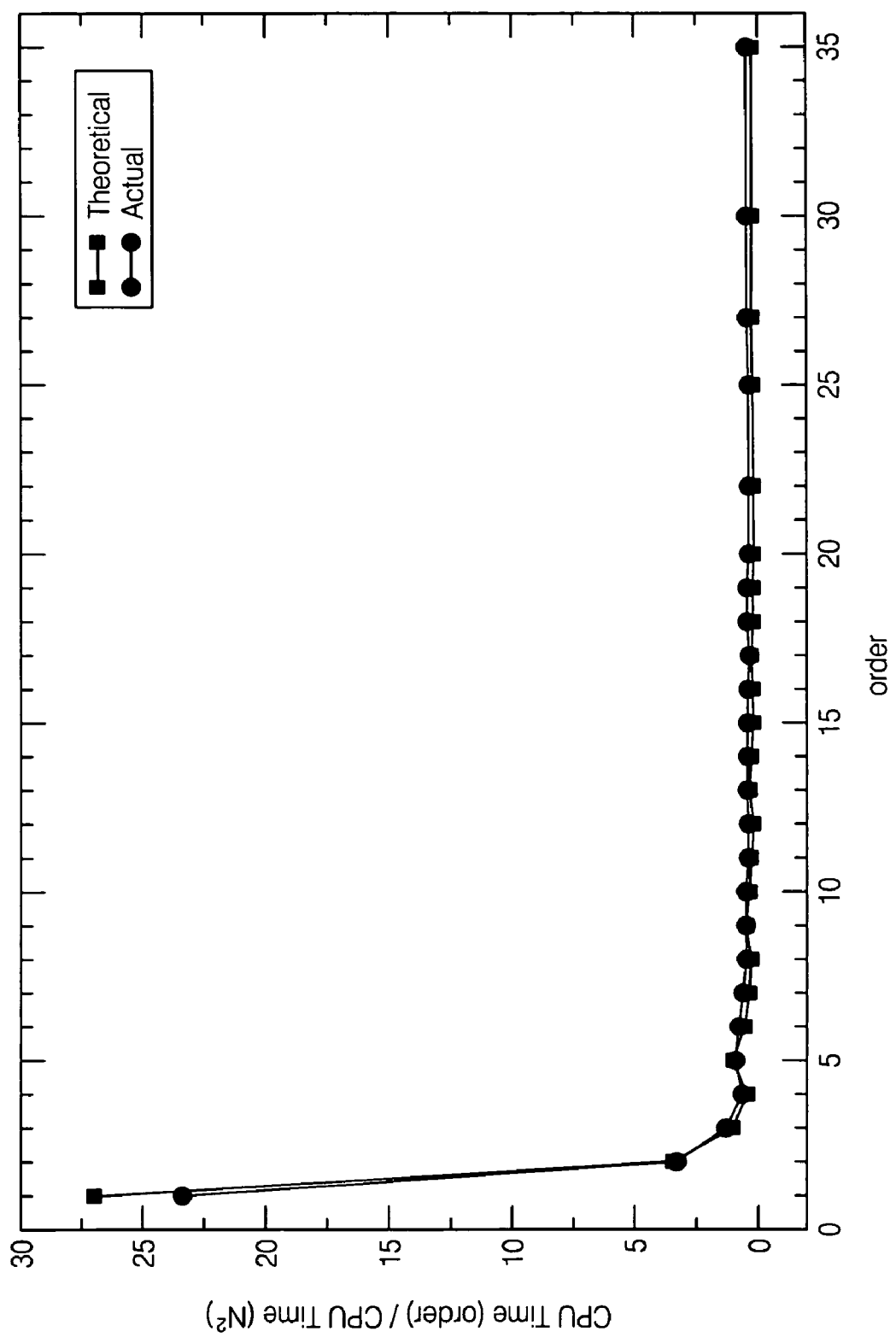
FIG. 11A is a graph illustrating a comparison between predicted cubic approximation and actual spherical approximation of binning results.
Figure 11B:
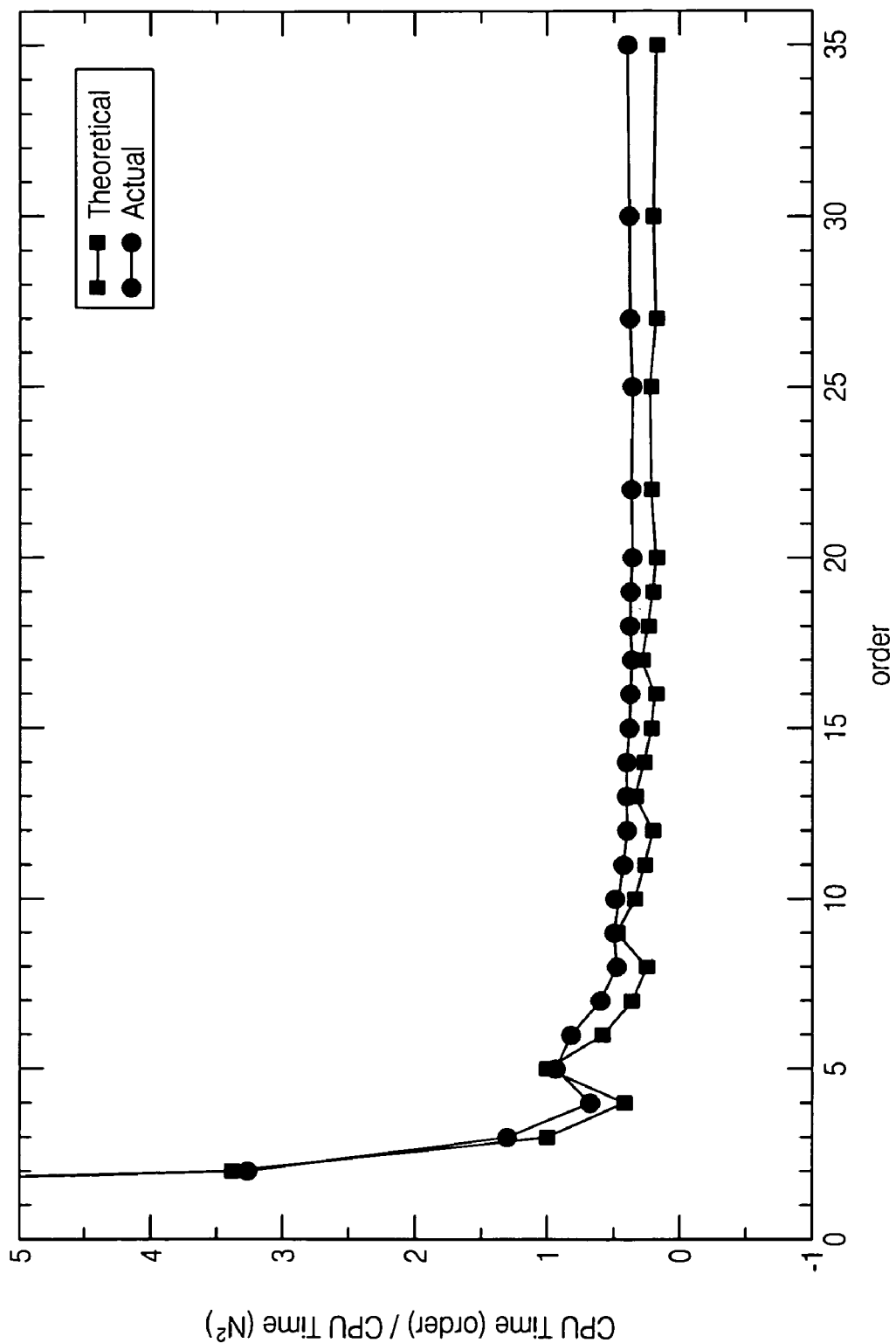
FIG. 11B is the graph of FIG. 11A on a modified scale.

FIGS. 11A and 11B show the results of these simulations. FIG. 11A shows all orders from 1 through 35, whereas FIG. 11B shows orders 2 through 35. The times given are normalized with the results from the simulation performed with the $N^2$ algorithm. For comparison, the predicted theoretical results are also shown for the orders tested, however, the predictions are based upon the cubic approximation binning, whereas the actual results were obtained using spherical approximation binning. Table 2 shows the same results in tabular format.

TABLE 2

| Order | Actual | Theoretical |
|---|---|---|
| 1 | 23.4 | 27.0 |
| 2 | 3.25 | 3.38 |
| 3 | 1.31 | 1.0 |
| 4 | 0.669 | 0.422 |
| 5 | 0.931 | 1.0 |
| 6 | 0.826 | 0.579 |
| 7 | 0.596 | 0.364 |
| 8 | 0.479 | 0.244 |
| 9 | 0.484 | 0.471 |
| 10 | 0.486 | 0.343 |
| 11 | 0.430 | 0.258 |
| 12 | 0.401 | 0.198 |
| 13 | 0.395 | 0.332 |
| 14 | 0.399 | 0.266 |
| 15 | 0.391 | 0.216 |
| 16 | 0.373 | 0.178 |
| 17 | 0.360 | 0.271 |
| 18 | 0.369 | 0.228 |
| 19 | 0.371 | 0.194 |
| 20 | 0.354 | 0.166 |
| 22 | 0.361 | 0.206 |
| 25 | 0.362 | 0.216 |
| 27 | 0.366 | 0.171 |
| 30 | 0.367 | 0.182 |
| 35 | 0.379 | 0.160 |

As predicted for this set of simulations, using o=[20, 20, 20] provided the fastest CPU time. For orders larger than 20, the average number of bodies per bin decreases below 1, and more CPU time was required to iterate over empty bins, whereas for orders under 20, more time was spent calculating interactions that are outside of the $r_{cutoff}$ and in iterating through linked lists. Thus, the optimal performance occurred, as predicted, by taking the order with the fastest theoretical time, and the lowest average number of bodies per bin, greater than or equal to one.

Scaling as a Function of N (Atoms in System)

The system used to test the scaling as a function of the number of atoms was done with parameters as specified in Table 3, as well as with $r_{cutoff}$=9 Å. In each case, the system was simulated using periodic boundary conditions and a group based cutoff, where each molecule of water contains only one binned parent atom. The orders used for each of the simulations show in Table 3 were selected by the binning optimizer routine. 2,500 Monte Carlo steps were attempted at 298K for each system shown, where each step involves either a center of mass rotation or a translation of each water molecule, using a 30% acceptance ration for both move types. The CPU time required to complete each simulation was measured.

TABLE 3

| N (TIP3P Molecules) | N (Atoms) | L (Å) | Order Vector |
|---|---|---|---|
| 216 | 648 | 18.63 | [6, 6, 6] |
| 512 | 1536 | 24.84 | [8, 8, 8] |
| 1728 | 5184 | 37.26 | [12, 12, 12] |
| 4096 | 12288 | 49.68 | [11, 16, 22] |
| 8000 | 24000 | 62.13 | [20, 20, 20] |

All simulations were performed with v. 3332 of ZymeCAD and compiled with full optimization using the gcc compiler. The processor used for these simulations was a 2.2 GHz AMD Athlon 64 with a cache size of 512 KB.

Figure 12:
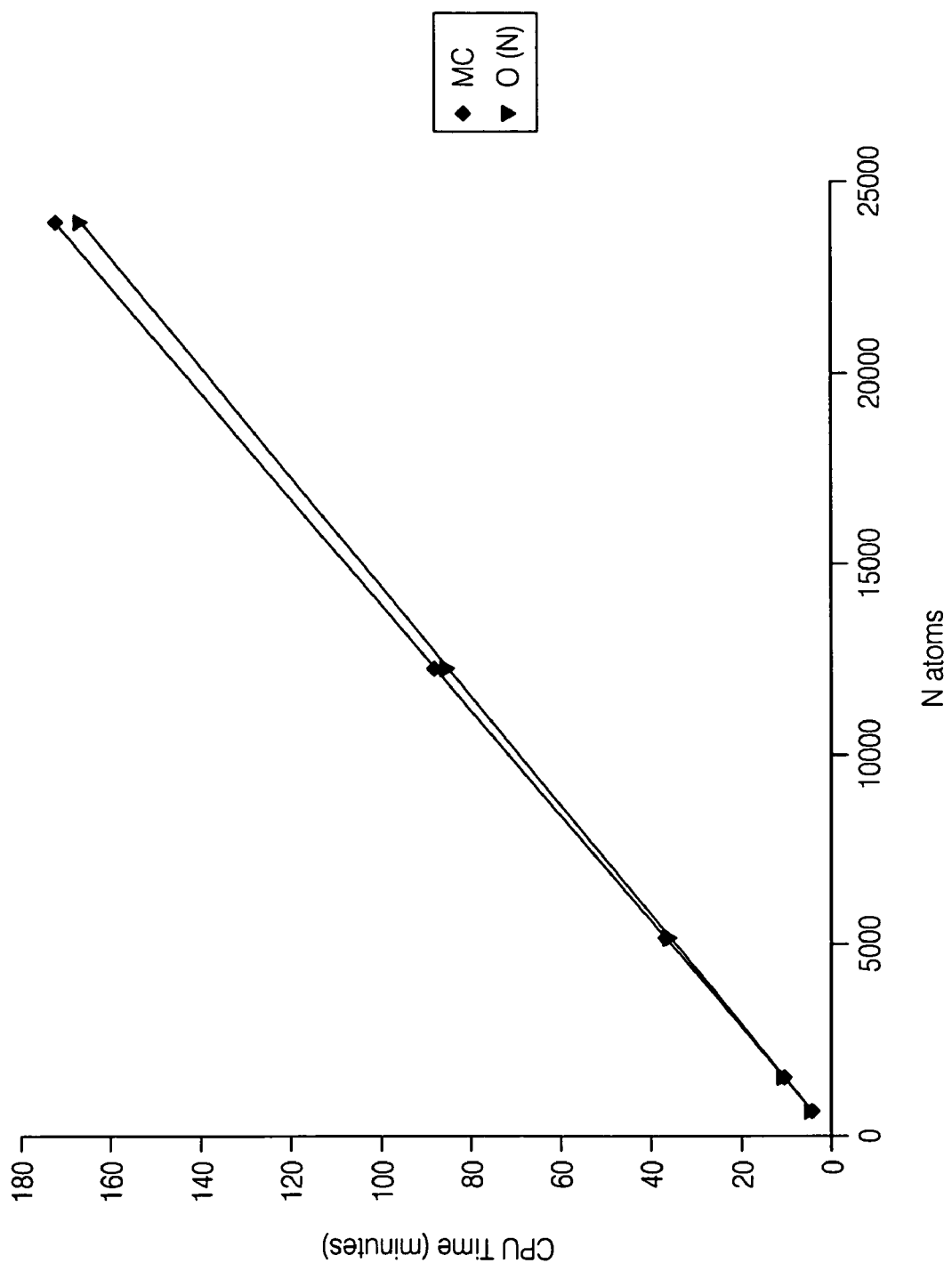
FIG. 12 is a graph comparing an expected processing time with an actual processing time.

FIG. 12 shows the results obtained, and Table 4 shows the same results in tabular format. For comparison, the expected CPU Time for O(N) performance is also shown, where the CPU time from the simulation with 216 TIP3P molecules is used to extrapolate the values. It can be seen clearly from this plot that binning algorithm scales as O(N).

TABLE 4

| N atoms | CPU Time Required | Extrapolated O(N) |
|---|---|---|
| 648 | 4.500 | 4.500 |
| 1536 | 10.818 | 10.667 |
| 5184 | 36.784 | 36.000 |
| 12288 | 88.531 | 85.333 |
| 24000 | 172.600 | 166.667 |

One consideration for the optimization of the binning method in the implementation given above, which does not apply to all implementations, is the speed of the memory access. In the device, as implemented in Appendices A through C, the bins are composed of a linked list memory structure, in which consecutive elements of the linked list are not likely to be contiguous in memory. Thus, traversing the linked list may result in slower access time than would be found in visiting contiguous addresses in an array structure.

Because moving to the head of a linked list is rapid, in terms of memory usage (the location of the head of each linked list is easily found in memory, and is likely to be pre-cached), moving between bins appears to be faster than moving through a single bin. Thus, the observed performance for a system of fixed size appears to increase as the number of bins increases, because of the decreasing length of the linked lists in each bin. However, this observed increase in performance eventually tapers off as the average length of the linked lists begins to decrease below 1. Once this occurs, the system begins to experience delays from the overhead in searching through an increased number of empty bins.

Thus, the observed optimal performance can be found by solving for the scaling equation given above (17), constrained by the average number of bodies in each bin being greater than or equal to 1. The binning optimizer takes this into consideration. This also differs from previous algorithms (see Quentrec and Brot, New Method for Searching for Neighbors in Molecular Dynamics Computations, *Journal of Computational Physics,* 13:430-432 (1973), which is hereby incorporated by reference in its entirety), where the number of bodies per bin set at a maximum of one.

A Method for Retrieving Specific Information from a Larger Data Set

The binning method can be used for indexing and storing information for other applications. When a large volume of data can be stored, retrieving the data often requires an efficient method of indexing the data, to reduce the access time. The binning method is adaptable to store other forms of data, including geographically relevant data, astronomical data, or any spatially correlated information. A further advantage can be obtained with the binning optimizer, in order to re-adjust the contents of the search at any point, making the method flexible and adaptable for dynamic data sets.

CONCLUSION

It will be appreciated by those skilled in the art that various modifications and changes may be made without departing from the scope of the invention. Such modifications and changes are intended to fall within the scope of the invention, as defined by the appended claims.

APPENDIX A

```
#ifndef __NBLIST_H__
#define __NBLIST_H__
#include "structures/system.h"
#include "structures/particle.h"
#include "lib/3d/vector.h"
/// This declaration is required for compilation
typedef struct bin_fill_node* bin_node_ptr;
/// The molecule/atom tuples.
typedef struct bin_fill_node {
    /// The molecule number
    int molecule;
    /// The atom number
    int atom;
    /// The wrap vector - Stores the relationship between the actual particle
    /// coordinates and the image of the coordinates in the system
    Vectorc wrap;
    /// The next node in the list (NULL for last node)
    bin_node_ptr next_node;
} bin_fill_node_t;
/// A single cell element.
typedef struct {
    /// The first node in the fill linked list. NULL for empty list
    bin_fill_node_t *head_node;
} bin_t;
/// A binning set for a class of atoms (MC, MD)
typedef struct {
    /// 1-D array of cells
    bin_t *bins;
    /// Actual storage of all fill_node_t
    /// This list is not in order of bins, and always represents a contigous portion
    /// of memory - used for allocation and faster rebinning
    bin_fill_node_t *fill_list;
    /// Number of nodes in the fill list
    int fill_list_size;
} bin_set_t;
/// The entire simulation space containing many cells.
typedef struct {
    /// The MC & MD binning sets - contain cells and nodes
    bin_set_t MC, MD;
    /// The number of cells in each dimension
    Vectori order;
    /// The total number of cells
    int order3;
    /// The dimensions of the bins. This is a vector of doubles so that
    /// cell_width * order = sytem_width.
    Vectord bin_width;
    /// The map - Read by the integrator
    Vectorc *map;
    /// Size of the map
    int map_size;
    /// Size of half the map - used to prevent iterating over the same cell twice
    int map_loc_zero_elem;
} bin_manager_t;
```

APPENDIX A-continued

```
/// The linked list iterator
typedef struct {
    /// The current node
    bin_fill_node_t *cur_node;
} bin_list_iter_t;
void bin_fill_list_iter_next (bin_list_iter_t *it);
char bin_fill_list_iter_end (bin_list_iter_t *it);
void bin_fill_list_iter_begin (bin_list_iter_t *it, bin_fill_node_t *start_node);
void bin_fill_list_iter_cur (const bin_list_iter_t *it, int *mol, int *atom,
                             Vectorc *wrap);
/// The neighbor list iterator
typedef struct {
    // The location of the root bin, in [x,y,z] representation
    Vectori root_bin_loc;
    /// The current bin this iterator is on.
    int cur_cell;
    /// The offset in the neighbor map we are at.
    int nb_offset;
    /// The bound at which we stop iterating over neighboring bins.
    int nb_bound;
    /// The fill list iterator for iterating through each cell
    bin_list_iter_t fill_iter;
    /// The last calculated shiftvector - save to retrieve with get_cur( )
    Vectorc shiftvector;
} bin_iter_t;
void bin_iter_begin (const bin_manager_t *bm, const bin_set_t *set,int cell,
                     bin_iter_t *it, int bound);
void bin_iter_next (const bin_manager_t *bm, const bin_set_t *set, bin_iter_t *it);
void bin_iter_get_cur (const bin_iter_t *it, int *mol, int *atom, Vectorc *wrap,
                       Vectorc *shiftvector);
char bin_iter_end (bin_iter_t *it);
bin_manager_t *bin_init (const system_t *sys, const Vectori *in_order);
void bin_deinit (bin_manager_t *bm);
void bin_calc_cell_width (Vectord *cell_width, const Vector *system_width,
                          const Vectori *order);
int bin_cell_ijk2idx_wrap (const bin_manager_t *bm, particle_t *atom,
                           const Vector *system_width, Vectorc *wrap);
void bin_do_bin_system (const bin_manager_t *bm, const system_t *sys,
                        const bin_set_t *set);
void bin_atom_bin_check (const bin_manager_t *bm, const system_t *sys, bin_set_t *set,
                         int mol, int *parent_atom_cell);
#endif
```

APPENDIX B

```
#include "bin.h"
#include "futils.h"
#define DBG_DOMAIN_THIS_FILE DBG_NBLIST
// Binning Set management ---------------------------------------------
static
void bin_set_init (const system_t *sys, bin_set_t *set, int order3,
                   int mol_start, int mol_finish);
void bin_set_deinit (bin_set_t *set);
// Bin management -----------------------------------------------------
static
void bin_clear_bins (const bin_manager_t *bm, bin_t *cells);
static
void bin_do_bin_parent_atom (const bin_manager_t *bm, const system_t *sys,
                             const bin_set_t *set);
static
void bin_do_rebin_atom (const bin_manager_t *bm, bin_t *cells,
                        int mol, int atom, Vectorc wrap, int n_orig_cell,
                        int n_new_cell);
// Map Routines -------------------------------------------------------
static
int bin_map_init (const system_t *sys, const Vectori *order, const Vectord *cell_width,
                  int *num_cells, Vectorc *final_map);
static inline int bin_map_ijk2int(const Vectori *p, const Vectori *order);
static int bin_map_wrap_move_to_int (const Vectorc *move, const Vectori *origin,
                                     const Vectori *order, Vectorc *shiftvector);
static inline void bin_map_int2ijk(int val, Vectori *result, const Vectori *order);
// Linked list Routines -----------------------------------------------
void bin_fill_list_init(const system_t *sys, bin_set_t *set, int mol_start, int mol_finish);
void bin_list_remove_node (bin_fill_node_t **head_node,
                           bin_fill_node_t *cur_node, bin_fill_node_t *prev_node);
```

APPENDIX B-continued

```
void bin_list_add_node (bin_fill_node_t **head_node, bin_fill_node_t *new_node);
bin_manager_t *bin_init (const system_t *sys, const Vectori *in_order)
{
  float num_neigh_cells;
  bin_manager_t *bm;
  int i;
  bm = zmalloc (sizeof (bin_manager_t));
  memset (bm, 0, sizeof (bin_manager_t));
  bm->order3 = 1;
  for (i = 0; i < 3; i++) {
    // Check if order in each component is larger than 1,
    // also done in zdb_init
    assert (in_order->m[i] >= 1);
    bm->order3 *= in_order->m[i]; //order ^3
  }
  vectori_copy (&bm->order, in_order);
  vectori_print(&bm->order, "Binning order");
  bin_calc_cell_width (&bm->bin_width, sys->system_width, &bm->order);
  num_neigh_cells = 1.0F;
  for (i = 0; i < 3; i++) {
    num_neigh_cells *= (int)(ceil (sqrt (sys->switch_max_squared)
                  / bm->bin_width.m[i])) * 2 + 1;
  }
  bin_set_init (sys, &bm->MD, bm->order3, 0, sys->MD_molecules);
  //Create the cell map
  //Allocate for maximal possible size of map
  bm->map = zmalloc(sizeof(Vectorc) * num_neigh_cells);
  // initialize the map and map size
  bm->map_loc_zero_elem =
    bin_map_init (sys, &bm->order, &bm->bin_width, &bm->map_size, bm->map);
  //Reallocate map to it's actual size - not known a-priori with
  // Spherical binning
  bm->map = realloc (bm->map, sizeof(Vectorc)*bm->map_size);
  return bm;
}
void bin_deinit (bin_manager_t *bm)
{
  bin_set_deinit (&bm->MD);
  free (bm->map);
  free (bm);
}
static
void bin_set_init (const system_t *sys, bin_set_t *set, int order3,
            int mol_start, int mol_finish)
{
  set->bins = zmalloc (sizeof(bin_t) * order3);
  if (set->bins == NULL) {
    debug (DBG_L1, "Out of memory");
  }
  memset (set->bins, 0, sizeof(bin_t) * order3);
  bin_fill_list_init(sys, set, mol_start, mol_finish);
}
void bin_set_deinit (bin_set_t *set)
{
  // do not assert set != NULL
  if (set != NULL) {
    free(set->bins);
    free(set->fill_list);
  }
}
void bin_fill_list_init(const system_t *sys, bin_set_t *set, int mol_start, int mol_finish)
{
  int atom, mol, count, size;
  bin_fill_node_t *list;
  count = 0;
  // Get the number of parent atoms for this region
  size = system_get_total_parent_atoms(sys, mol_start, mol_finish);
  list = zmalloc (sizeof(bin_fill_node_t) * size);
  memset(list, 0, sizeof(bin_fill_node_t) * size);
  for (mol = mol_start; mol < mol_finish; mol++) {
    for (atom = 0; atom < sys->MOLECULES[mol]->total_atoms; atom++) {
      if (sys->MOLECULES[mol]->ATOMS[atom]->is_parent) {
        list[count].atom = atom;
        list[count].molecule = mol;
```

APPENDIX B-continued

```
            //Calc initial wrap vector
            // wrap = ...
            count ++;
          }
        }
      }
    }
    set->fill_list = list;
    set->fill_list_size = count;
}
void bin_atom_bin_check (const bin_manager_t *bm, const system_t *sys, bin_set_t *set,
                int mol, int *parent_atom_cell)
{
    int new_cell, parent_atom;
    Vectorc wrap;
    parent_atom = FIRST_PARENT_ATOM_IN_GROUP;
    new_cell = bin_cell_ijk2idx_wrap (bm, sys->MOLECULES[mol]-
>ATOMS[parent_atom],
                        sys->system_width, &wrap);
    bin_do_rebin_atom (bm, set->bins, mol, parent_atom, wrap, *parent_atom_cell,
                new_cell);
    *parent_atom_cell = new_cell;
}
static
void bin_clear_bins (const bin_manager_t *bm, bin_t *cells)
{
    int i;
    for (i = 0; i < bm->order3; i++) {
        cells[i].head_node = NULL;
    }
}
static
void bin_do_bin_parent_atom (const bin_manager_t *bm, const system_t *sys,
                    const bin_set_t *set)
{
    int ibin, j;
    Vectorc wrap;
    bin_fill_node_t *cur_node;
    for (j = set->fill_list_size; j > 0; j--) {
        cur_node = &set->fill_list[j-1];
        ibin = bin_cell_ijk2idx_wrap (bm,
            sys->MOLECULES[cur_node->molecule]->ATOMS[cur_node->atom],
                        sys->system_width, &wrap);
        //Only the wrap vector and cell location should be updated -
        // atom and mol number don't change, node is simply "moved"
        cur_node->wrap = wrap;
        bin_list_add_node(&(set->bins[ibin].head_node), cur_node);
    }
}
void bin_do_bin_system (const bin_manager_t *bm, const system_t *sys,
                const bin_set_t *set)
{
    bin_clear_bins (bm, set->bins);
    bin_do_bin_parent_atom (bm, sys, set);
}
void bin_list_remove_node (bin_fill_node_t **head_node, bin_fill_node_t *cur_node,
bin_fill_node_t *prev_node)
{
    if (prev_node == NULL) {
        //special case for removing first node
        assert (*head_node == cur_node);
        *head_node = cur_node->next_node;
    } else {
        prev_node->next_node = cur_node->next_node;
    }
    // Ensure cur_node doesn't point inside the old fill list
    cur_node->next_node = NULL;
}
void bin_list_add_node (bin_fill_node_t **head_node, bin_fill_node_t *new_node)
{
    bin_fill_node_t *temp_ptr;
    //Old head of the list
    temp_ptr = *head_node;
    //Push the new node to the front
    *head_node = new_node;
    // Reattach the rest of the list to the new head
    new_node->next_node = temp_ptr;
}
```

APPENDIX B-continued

```
void bin_fill_list_iter_next (bin_list_iter_t *it)
{
  it->cur_node = it->cur_node->next_node;
}
char bin_fill_list_iter_end (bin_list_iter_t *it)
{
  return (it->cur_node == NULL);
}
void bin_fill_list_iter_cur (const bin_list_iter_t *it, int *mol, int *atom,
                             Vectorc *wrap)
{
  bin_fill_node_t *node;
  node = it->cur_node;
  *mol = node->molecule;
  *atom = node->atom;
  *wrap = node->wrap;
}
void bin_fill_list_iter_begin (bin_list_iter_t *it, bin_fill_node_t *start_node)
{
  it->cur_node = start_node;
}
static
void bin_do_rebin_atom (const bin_manager_t *bm, bin_t *cells,
                        int mol, int atom, Vectorc wrap, int n_orig_cell,
                        int n_new_cell)
{
  bin_fill_node_t *cur_node, *prev_node;
  bin_t *orig_cell, *new_cell;
  orig_cell = &cells[n_orig_cell];
  new_cell = &cells[n_new_cell];
  //Find the entry for this atom within the original cell
  cur_node = orig_cell->head_node;
  prev_node = NULL;
  while (cur_node != NULL && (cur_node->molecule != mol || cur_node->atom != atom) )
  {
      prev_node = cur_node;
      cur_node = cur_node->next_node;
  }
  if (cur_node != NULL) {
    cur_node->wrap = wrap;
    bin_list_remove_node(&(orig_cell->head_node), cur_node, prev_node);
    bin_list_add_node(&(new_cell->head_node), cur_node);
  } else {
    //Add details
    debug(DBG_L1, "Rebin - Atom not found in original cells\n");
  }
}
void bin_calc_cell_width (Vectord *cell_width, const Vector *system_width,
                          const Vectori *order)
{
  Vectord system_widthd, orderd;
  int i;
  vector_to_vectord (system_width, &system_widthd);
  vectori_to_vectord (order, &orderd);
  for (i = 0; i < 3; i++) {
     cell_width->m[i] = system_widthd.m[i] / (double) order->m[i];
  }
}
int bin_cell_ijk2idx_wrap (const bin_manager_t *bm, particle_t *atom,
                           const Vector *system_width, Vectorc *wrap)
{
  Vector *coord, orig_coord;
  Vectori tmp;
  int ret, i;
  // Copy the particle coords
  coord = point_particle_coords (atom);
  vector_copy (&orig_coord, coord);
  // Wrap the particle inside the system bounds
  fold_to_vectorc (0, 0, 0, 0, wrap);
  particle_wrap_into_system (atom, system_width, wrap);
  // Get the cell number of the atom within the system bounds
  for (i = 0; i < 3; i++) {
     tmp.m[i] = (int) (coord->m[i] / bm->bin_width.m[i]);
     assert (tmp.m[i] >= 0 && tmp.m[i] < bm->order.m[i]);
  }
```

APPENDIX B-continued

```
    ret = bin_map_ijk2int (&tmp, &bm->order);
    // Put the particle back in its original position
    vector_copy (coord, &orig_coord);
    return ret;
}
// END BIN SECTION
========================================================
// START MAP SECTION
========================================================
static int bin_map_init (const system_t *sys, const Vectori *order, const Vectord *cell_width,
                int *num_cells, Vectorc *final_map)
{
    // Number of cells in the map
    int count;
    // loop counters
    int i,j,k,abs_i,abs_j,abs_k;
    double rcutoff;
    float dist_x, dist_y, dist_z;
    Vector *system_width, cell_width_squared, box_bounds;
    rcutoff = sqrt(sys->switch_max_squared);
    system-width = sys->system_width;
    count = 0;
    vectord_to_vector(cell_width, &cell_width_squared);
    vector_multiply(&cell_width_squared, &cell_width_squared, &cell_width_squared);
    for (i=0; i<3; i++) {
        box_bounds.m[i] = ceilf (rcutoff / cell_width->m[i]);
    }
    for (i = -box_bounds.m[2]; i <= box_bounds.m[2]; i++) {
        abs_i = abs(i);
        if (abs_i > 1) {
            dist_z = (abs_i-1)*(abs_i-1)*cell_width_squared.m[2];
        } else {
            dist_z = 0;
        }
        for (j = -box_bounds.m[1]; j <= box_bounds.m[1]; j++) {
            abs_j = abs(j);
            if (abs_j > 1) {
                dist_y = (abs_j-1)*(abs_j-1)*cell_width_squared.m[1];
            } else {
                dist_y = 0;
            }
            for (k = -box_bounds.m[0]; k <= box_bounds.m[0]; k++) {
                abs_k = abs(k);
                if (abs_k > 1) {
                    dist_x = (abs_k-1)*(abs_k-1)*cell_width_squared.m[0];
                } else {
                    dist_x = 0;
                }
                if (dist_x + dist_y + dist_z < sys->switch_max_squared)
                {
                    fold_to_vectorc((char)k, (char)j, (char)i, 0, &(final_map[count]));
                    count++;
                }
            }
        }
    }
    (*num_cells) = count;
    //The 0,0,0 element is always at 2n-1, by symmetry around +/- each axis.
    return (count-1)/2;
}
static int bin_map_wrap_move_to_int (const Vectorc *move, const Vectori *origin,
                    const Vectori *order, Vectorc *shiftvector)
{
    Vectori temp;
    int i;
    // Cast
    vectorc_to_vectori(&temp, move);
    // Do the move
    vectori_add (&temp, origin, &temp);
    // Wrap around
    for (i = 0; i < 3; i++) {
        if (temp.m[i] >= order->m[i]) {
            shiftvector->m[i] = +1;
            temp.m[i] -= order->m[i];
```

APPENDIX B-continued

```
        } else if (temp.m[i] < 0) {
            shiftvector->m[i] = -1;
            temp.m[i] += order->m[i];
        }
        else {
            shiftvector->m[i] = 0;
        }
    }
    // Get the int value for this move
    return bin_map_ijk2int (&temp, order);
}
static inline int bin_map_ijk2int(const Vectori *p, const Vectori *order)
{
    return ( ( (p->m[2] * order->m[1]) + p->m[1]) * order->m[0] + p->m[0]);
}
static inline void bin_map_int2ijk(int val, Vectori *result, const Vectori *order)
{
    int temp;
    temp = (order->m[0] * order->m[1]);
    result->m[2] = (val / temp);
    val = val - temp * result->m[2];
    result->m[1] = (val / order->m[0]);
    result->m[0] = val - result->m[1] * order->m[0];
}
// END MAP SECTION
//======================================================
// START ITERATOR SECTION
//==============================================
void bin_iter_begin (const bin_manager_t *bm, const bin_set_t *set, int bin,
            bin_iter_t *it, int bound)
{
    // Initialize values of the iterator elements
    it->nb_offset = -1;
    it->nb_bound = bound;
    // Clear the fill list iterator
    it->fill_iter.cur_node = NULL;
    bin_map_int2ijk(bin, &it->root_bin_loc, &(bm->order) );
    if (!bin_iter_end(it))
        bin_iter_next (bm, set, it);
}
char bin_iter_end (bin_iter_t *it)
{
    // End the iterator when the last cell in the list is reached
    if (it->nb_offset == it->nb_bound) {
        return TRUE;
    }
    else {
        return FALSE;
    }
}
void bin_iter_get_cur (const bin_iter_t *it, int *mol, int *atom, Vectorc *wrap,
            Vectorc *shiftvector)
{
    bin_fill_list_iter_cur(&it->fill_iter, mol, atom, wrap);
    *shiftvector = it->shiftvector;
}
void bin_iter_next (const bin_manager_t *bm, const bin_set_t *set, bin_iter_t *it)
{
    bin_t *bins;
    bins = set->bins;
    // Go to the next node in this linked list
    if (!bin_fill_list_iter_end(&it->fill_iter)) {
        bin_fill_list_iter_next(&it->fill_iter);
        if (it->fill_iter.cur_node != NULL) {
            // Make sure this wasn't the last node in the fill list
            return;
        }
        // If end of fill list is reached, move on to new cell
    } //else, find a new cell
    // Increment the cell number offset
    it->nb_offset++;
    for (; it->nb_offset <it->nb_bound; it->nb_offset++) {
        // Get the next cell number
        it->cur_cell = bin_map_wrap_move_to_int(&(bm->map[it->nb_offset]),
                            &it->root_bin_loc, &(bm->order),
                            &it->shiftvector);
        // Break loop if cell is occupied
```

APPENDIX B-continued

```
        if (bins[it->cur_cell].head_node != NULL) {
            // Set up to begin iterating once we have a non empty bin
            bin_fill_list_iter_begin(&it->fill_iter, bins[it->cur_cell].head_node);
            break;
        }
    }
}
```

APPENDIX C

```
lib/3d/vector.h
#define NUM_D_VECTORD 3
/// Double Vector
typedef struct {
    /// Array of Doubles
    double m[NUM_D_VECTORD];
} Vectord;
typedef union {
    ///array of 4 characters
    char m[4];
} Vectorc;
typedef float v4sf __attribute__ ((vector_size(16)));
typedef union {
    /* Packed structure of 4 floats. */
    v4sf v;
    float m[4];
} Vector;
typedef union {
    v4si v;
    int m[4];
} Vectori;
structures/system.h
#define FIRST_PARENT_ATOM_IN_GROUP 0;
typedef struct {
    /// Array of pointers to all molecules in the system
    molecule_t **MOLECULES;
    /// The total number of MD and MC molecules in the system
    int total_molecules;
    /// The number of MD molecules in the system. In the molecule list,
    /// these molecules are listed first. If present, they are followed
    /// by MC_molecules, which is the number of molecules for which MC
    /// is being performed.
    int MD_molecules;
    /// The paramter file data
    parm_data_t *pd;
    /// The system width
    Vector *system_width;
    /// The cutoff distance squared at which all interactions are switched off
    /// DO NOT CHANGE TYPE - IT NEEDS TO BE A DOUBLE
    FOR BINNING double switch_max_squared;
    /// The cutoff distance squared at which the switching function is turned
    on float switch_min_squared;
    /// Flag indicating pbc TRUE or FALSE
    short pbc;
    /// Flag indicating binning TRUE or FALSE
    short bin;
    /// The simulation equilibrium temperature specified in *.in file
    /// in units of Kelvin
    float Teq;
    /// Teq * BOLTZMANN's constant in internal units
    float kT;
    /* DO NOT ADD ANYTHING TO THIS STRUCTURE UNLESS
    YOU ARE ABSOLUTLY SURE */
} system_t;
structures/particle.h
/// Particle structure holds the coordinates of the particle
typedef struct {
    /// Coordinates of the atom
    Vector coords;
} particle_t;
futils.h
#define zmalloc(size)
zmalloc_func(size, __func__, __FILE__, __LINE__)
```

APPENDIX C-continued

```
#define FALSE 0
#define TRUE 1
```

What is claimed is:

1. An optimized computerized method of determining interaction energies between bodies in a simulation space comprising:
   providing a simulation space comprising a plurality of bodies;
   dividing the simulation space into bins, wherein the number of bins with only one body is maximized wherein the number of bins is optimized by solving for a scaling equation constrained by the average number of bodies in each bin;
   selecting a radius for a first body in the simulation space at which an effect of a second body on the first body can be approximated to zero; and
   calculating the interaction energy of all bodies within the radius on the first body.

2. The method of claim 1, wherein the simulation space comprises at least two dimensions.

3. The method of claim 2, wherein the bins are of equal shape.

4. The method of claim 2, wherein the bins are of equal volume.

5. The method of claim 1, wherein the bins are selected to approximate a volume of a sphere with the radius.

6. The method of claim 1, further comprising providing a relative map that may be applied to any cell and wherein only one map is stored and wherein the one map comprises a list of relative positions of all neighbor bins over which an iterator may pass.

7. The method of claim 1, wherein the simulation space comprises non-cubic dimensions.

8. A computer readable medium comprising computer executable instructions that cause a computer to perform a method for optimizing system performance of an N-body problem comprising:
   providing a simulation space comprising a plurality of bodies;
   dividing the simulation space into bins, wherein the number of bins with only one body is maximized wherein the number of bins is optimized by solving for a scaling equation constrained by the average number of bodies in each bin;
   selecting a radius for a first body in the simulation space at which an effect of a second body on the first body can be approximated to zero; and
   calculating the interaction energy of all bodies within the radius on the first body.

9. The computer readable medium of claim 8, wherein the simulation space comprises at least two dimensions.

10. The computer readable medium of claim 9 wherein the bins are of equal shape.

11. The computer readable medium of claim 9, wherein the bins are of equal volume.

12. The computer readable medium of claim 8, wherein the bins are selected to approximate a volume of a sphere with the radius.

13. The computer readable medium of claim 8, further comprising providing a relative map that may be applied to any cell and wherein only one map is stored and wherein the one map comprises a list of relative positions of all neighbor bins over which an iterator may pass.

14. The computer readable medium of claim 8, wherein the simulation space comprises non-cubic dimensions.

15. A computer system for modeling interactions between bodies comprising:
 a system bus comprising a memory;
 a display;
 an I/O system;
 a storage;
 a first module configured to provide a simulation space comprising a plurality of bodies;
 a second module configured to divide the simulation space into bins, wherein the number of bins with only one body is maximized wherein the number of bins is optimized by solving for a scaling equation constrained by the average number of bodies in each bin;
 a third module configured to select a radius for a first body in the simulation space at which an effect of a second body on the first body can be approximated to zero; and
 a fourth module configured to calculate the interaction energies of all bodies within the radius on the first body.

16. The system of claim 15, wherein the simulation space comprises at least two dimensions.

17. The system of claim 16, wherein the bins are of equal shape.

18. The system of claim 16, wherein the bins are of equal volume.

19. The system of claim 16, wherein the simulation space comprises non-cubic dimensions.

* * * * *